(12) United States Patent
Entezari et al.

(10) Patent No.: US 11,232,612 B2
(45) Date of Patent: Jan. 25, 2022

(54) HIGHLY ACCURATE AND EFFICIENT FORWARD AND BACK PROJECTION METHODS FOR COMPUTED TOMOGRAPHY

(71) Applicant: University of Florida Research Foundation, Incorporated, Gainesville, FL (US)

(72) Inventors: Alireza Entezari, Gainesville, FL (US); Kai Zhang, Santa Clara, CA (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 23 days.

(21) Appl. No.: 16/817,946

(22) Filed: Mar. 13, 2020

(65) Prior Publication Data

US 2020/0294289 A1    Sep. 17, 2020

Related U.S. Application Data

(60) Provisional application No. 62/818,971, filed on Mar. 15, 2019.

(51) Int. Cl.
*G06K 9/00* (2006.01)
*G06T 11/00* (2006.01)
*G16H 30/40* (2018.01)

(52) U.S. Cl.
CPC ........... *G06T 11/008* (2013.01); *G16H 30/40* (2018.01)

(58) Field of Classification Search
CPC ............. G06T 11/008; G06T 2211/421; G06T 11/006; G16H 30/40
See application file for complete search history.

(56) References Cited

U.S. PATENT DOCUMENTS

| | | | | |
|---|---|---|---|---|
| 2009/0060299 | A1* | 3/2009 | Hibbard | G06T 17/30 382/128 |
| 2011/0194741 | A1* | 8/2011 | Ekin | G06T 7/0012 382/128 |
| 2012/0126125 | A1* | 5/2012 | Akazawa | A61B 6/037 250/363.04 |
| 2014/0119630 | A1* | 5/2014 | Sowards-Emmerd | A61B 6/5217 382/131 |
| 2014/0126793 | A1* | 5/2014 | Ahn | G06T 11/006 382/131 |
| 2014/0307934 | A1* | 10/2014 | Batenburg | G06T 11/005 382/131 |
| 2016/0300369 | A1* | 10/2016 | Silver | G06T 5/20 |

OTHER PUBLICATIONS

Alireza, ("A Box Spline Calculus for the Discretization of Computed Tomography Reconstruction Problems", IEEE Transactions on medical imaging, vol. 31, No. 8, Aug. 2012) (Year: 2012).*

* cited by examiner

*Primary Examiner* — Amara Abdi
(74) *Attorney, Agent, or Firm* — Alston & Bird LLP

(57) ABSTRACT

An image is reconstructed an image from projection data by an image reconstruction computing entity. Projection data captured by an imaging device is received. An image is reconstructed and/or generated based at least in part on the projection data using a forward and back projection technique employing a convolutional spline process. The image is provided such that a user computing entity receives the image. The user computing entity is configured to display the image via a user interface thereof.

20 Claims, 17 Drawing Sheets

HIGHLY ACCURATE AND EFFICIENT FORWARD AND BACK PROJECTION METHODS FOR COMPUTED TOMOGRAPHY

CROSS-REFERENCE TO RELATED APPLICATIONS

This application claims priority to U.S. Application No. 62/818,971, filed Mar. 15, 2019, the content of which is incorporated herein by reference in its entirety.

FEDERALLY SPONSORED RESEARCH OR DEVELOPMENT

This invention was made with government support under 1617101 awarded by National Science Foundation and N00014-14-1-0762 awarded by the U.S. Navy Office of Naval Research. The government has certain rights in the invention.

BACKGROUND

Biomedical imaging modalities use principles of Computed Tomography (CT) and tomographic reconstruction algorithms to form 2-D or 3-D images from projection data (e.g., X-ray CT, Positron Emission Tomography (PET), Single Photon Emission Computed Tomography (SPECT), and/or other projection data). To minimize patients' exposure to harmful ionizing X-ray radiations, modern algorithms—known as iterative reconstruction—enable image reconstruction from low-dose radiation with quality comparable to those obtained from high-dose radiation and reconstructed by classical algorithms. While the research over last three decades has produced a number of promising iterative reconstruction algorithms, their translation to practical settings (e.g., clinical settings) and commercial scanners has not been successful. The main impediment to this progress has been the computational cost to these iterative algorithms. For example, currently available scanners can take up to 90 minutes in clinical settings in spite of having access to ample parallel computing resources (e.g., multi-GPU and CPU cores). The long reconstruction time has made iterative reconstruction a commercial failure. As a result, the classical Filtered Back Projection (FBP) algorithm, and its variants, are widely used in practice, which require higher dose imaging techniques.

BRIEF SUMMARY OF SOME EXAMPLE EMBODIMENTS

An example embodiment of the present invention provides reconstructs and/or generates an image based on projection information/data using a forward and back projection technique that employs a convolutional spline process. The convolution spline process comprises using a box spline basis set for a footprint and/or detector blur computation used to generate and/or reconstruct the image. The projection information/data is captured by an imaging device via an imaging process such as X-ray CT, PET, SPECT, and/or the like. The projection information/data is captured using a low-dose, few view, and/or limited view technique that reduces the amount of radiation experienced by the individual (e.g., patient, study participant, and/or the like) being imaged. The image is provided to a user computing entity such that the user computing entity may display the image via a user interface thereof. In various embodiments, the image is provided within ten minutes of the projection information/data being received by the image reconstruction computing entity. Various embodiments provided a faster and more accurate image generation and/or reconstruction than methods known in the art (e.g., separable footprint (SF), look-up table-based ray integration (LTRI)).

According to a first aspect of the present disclosure, a method for reconstructing an image from projection data by an image reconstruction computing entity is provided. In an example embodiment, the method comprises receiving, by the image reconstruction computing entity, projection data captured by an imaging device; reconstructing, by the image reconstruction computing entity, an image based at least in part on the projection data using a forward and back projection technique employing a convolutional spline process; and providing, by the image reconstruction computing entity, the image such that a user computing entity receives the image, the user computing entity configured to display the image via a user interface thereof.

According to another aspect of the present disclosure, an apparatus configured to reconstruct an image from projection data captured by an imaging device is provided. In an example embodiment, the apparatus comprises at least one processor, a communications interface configured for communicating via at least one network, and at least one memory storing computer program code. The at least one memory and the computer program code configured to, with the processor, cause the apparatus to at least receive projection data captured by an imaging device; reconstruct an image based at least in part on the projection data using a forward and back projection technique employing a convolutional spline process; and provide the image such that a user computing entity receives the image, the user computing entity configured to display the image via a user interface thereof.

According to still another aspect of the present disclosure a computer program product configured to cause an apparatus to reconstruct an image from projection data captured by an imaging device is provided. In an example embodiment, the computer program product comprises at least one non-transitory computer-readable storage medium having computer-readable program code portions stored therein. The computer-readable program code portions comprise executable portions configured, when executed by a processor of an apparatus, to cause the apparatus to receive projection data captured by an imaging device; reconstruct an image based at least in part on the projection data using a forward and back projection technique employing a convolutional spline process; and provide the image such that a user computing entity receives the image, the user computing entity configured to display the image via a user interface thereof.

BRIEF DESCRIPTION OF THE DRAWINGS

Figure 1:
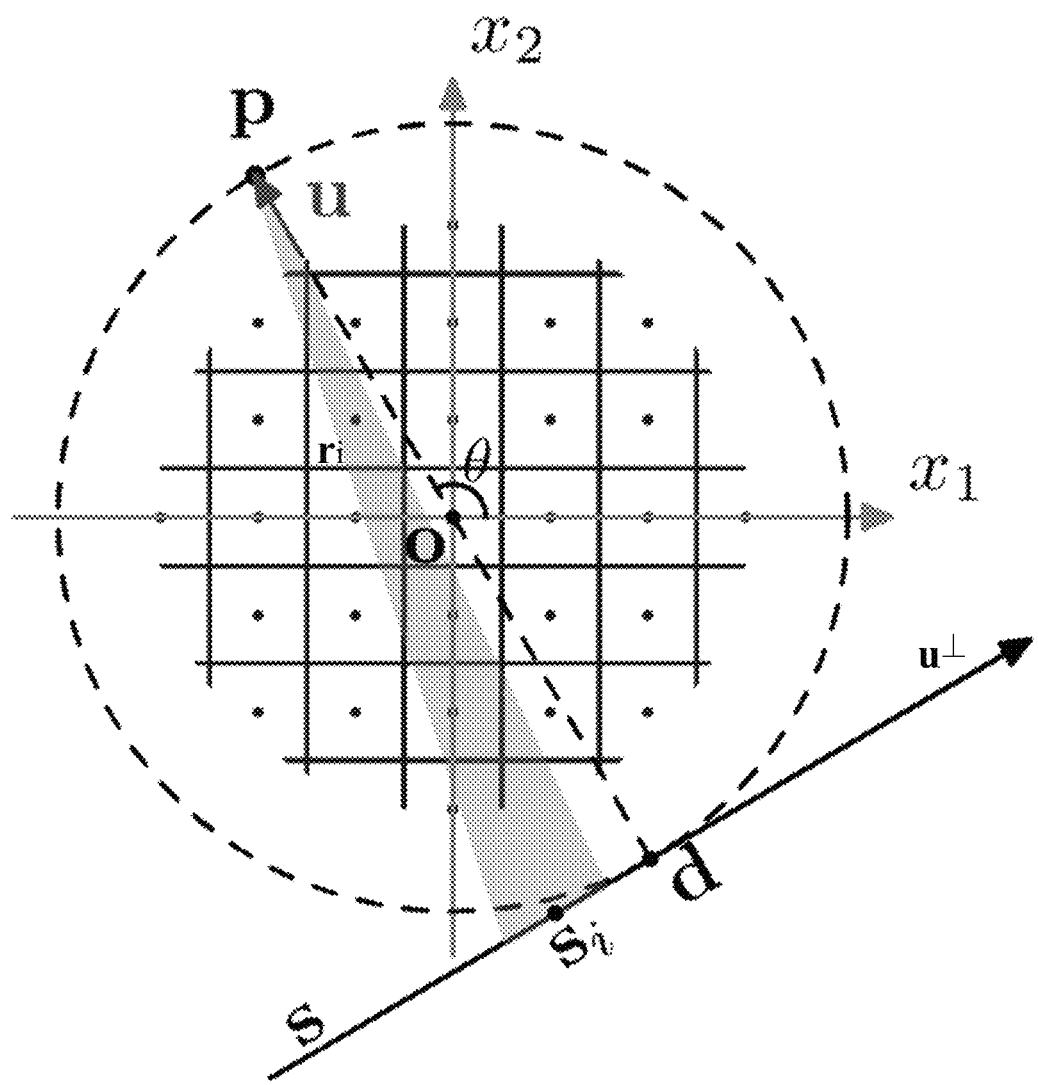
Figure 2:
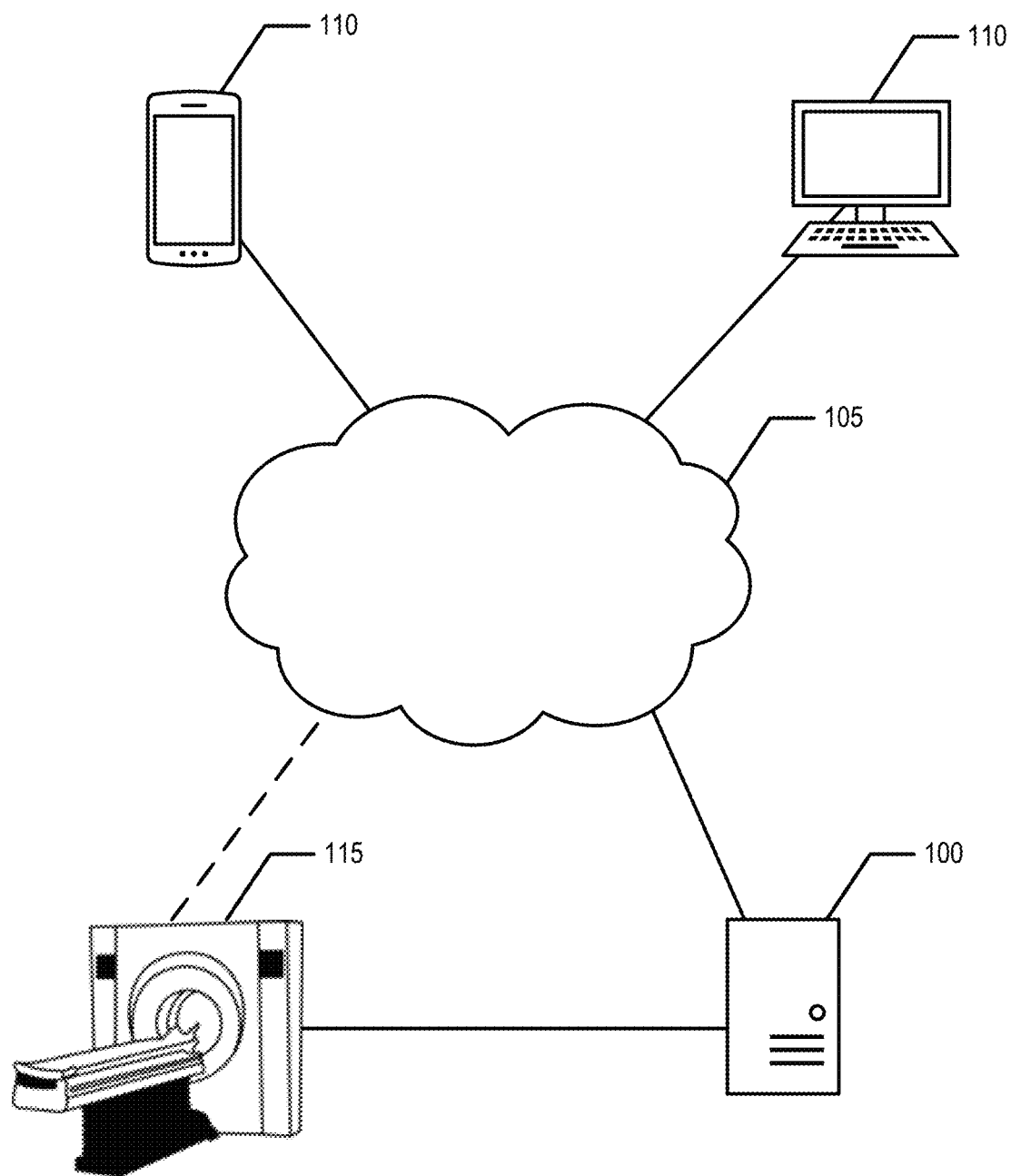
Figure 3:
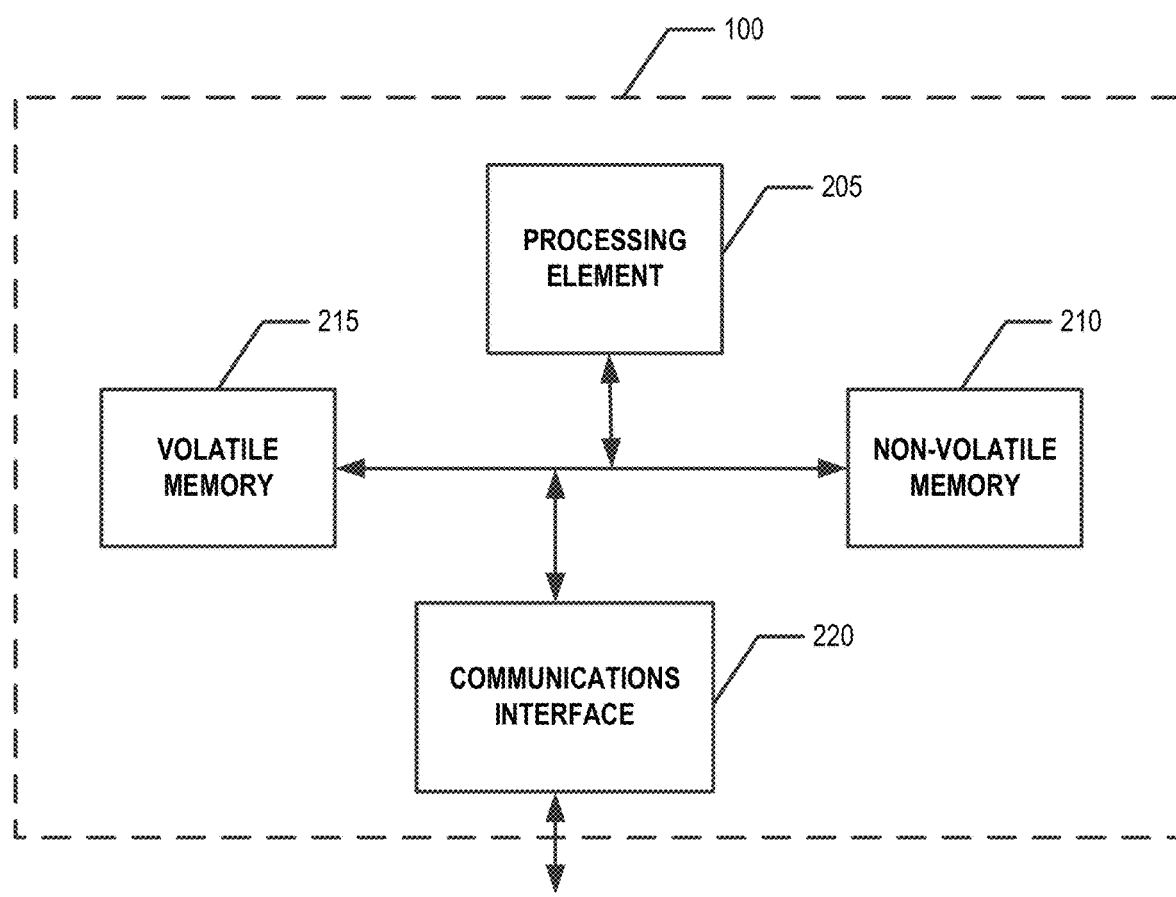
Figure 4:
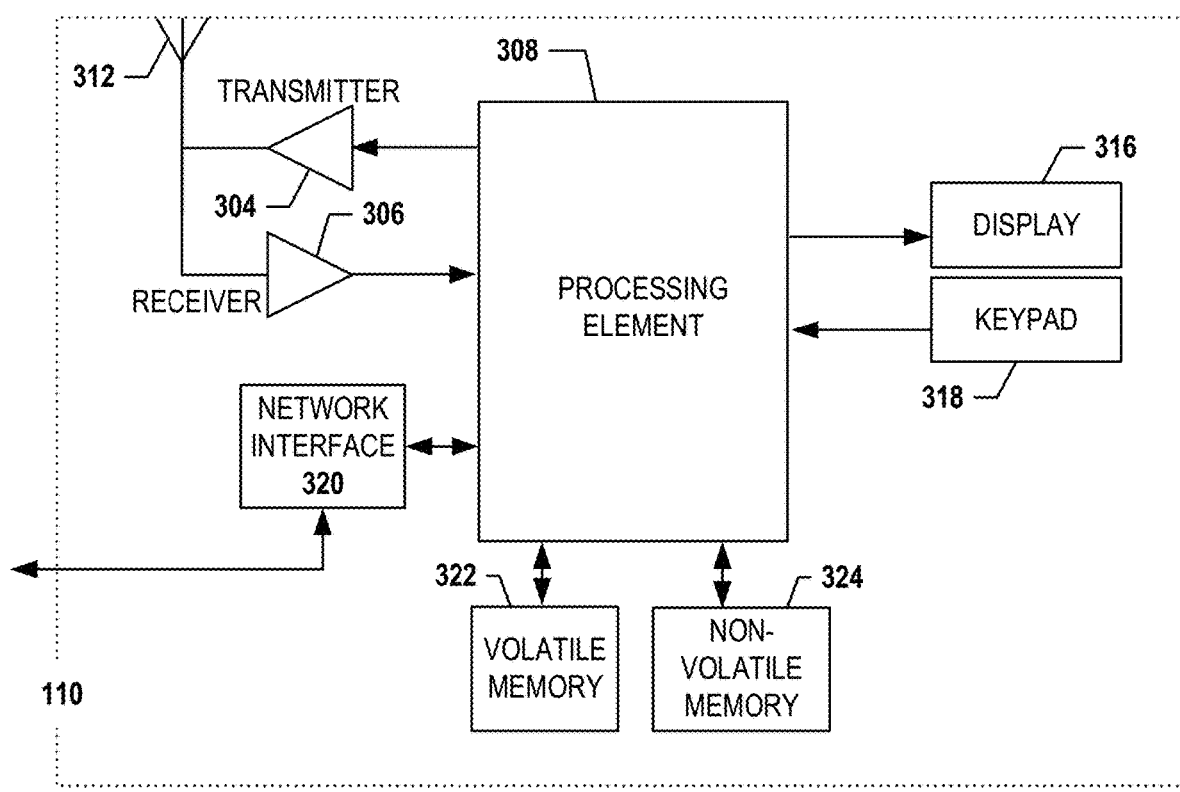
Figure 5:
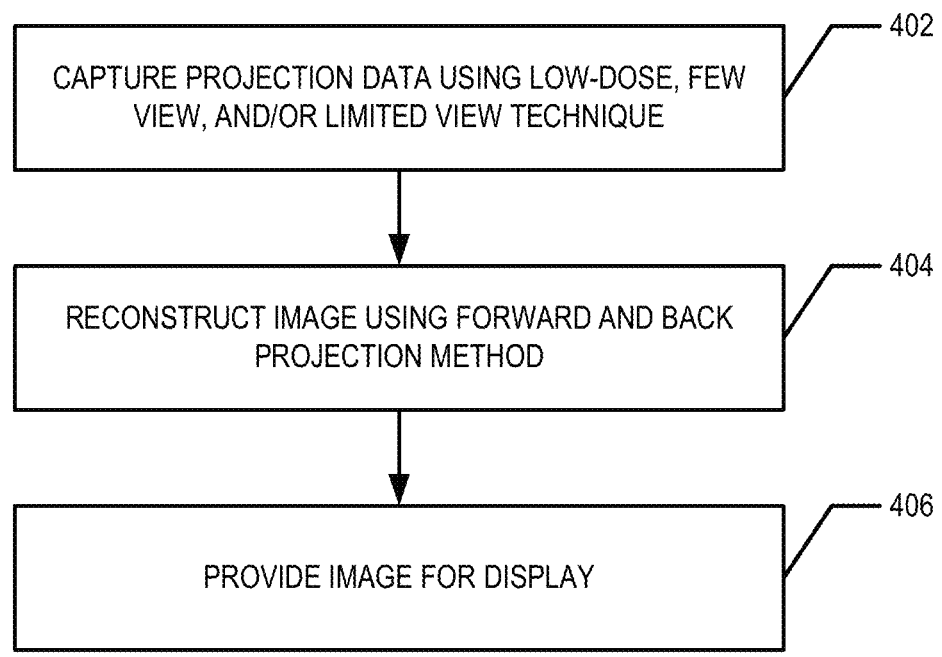
Figure 6:
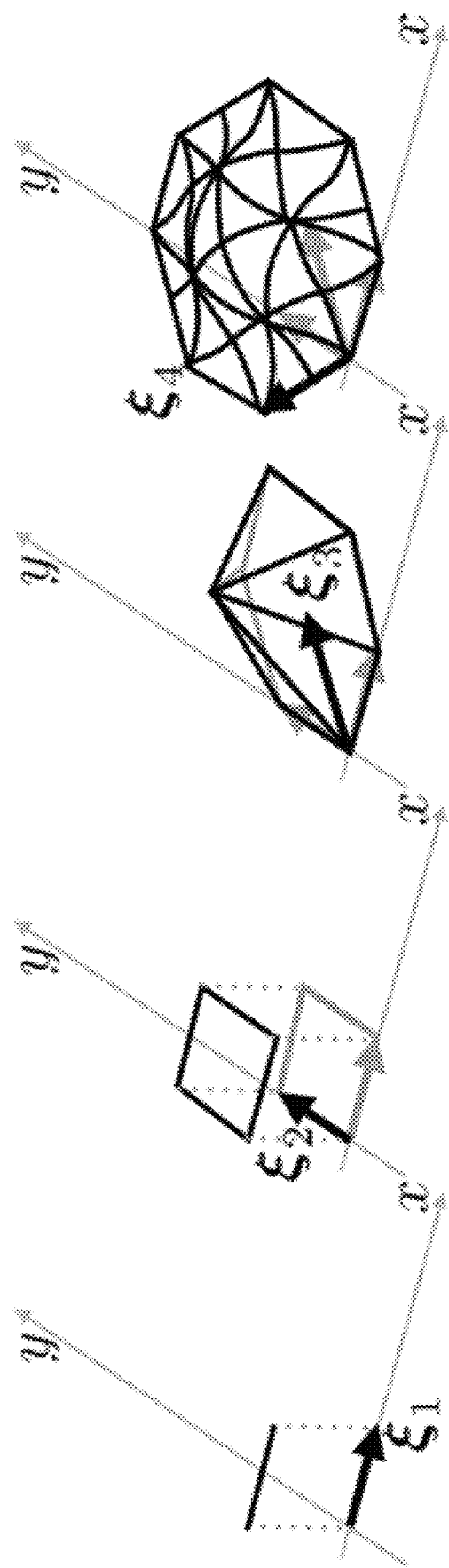
Figure 7:
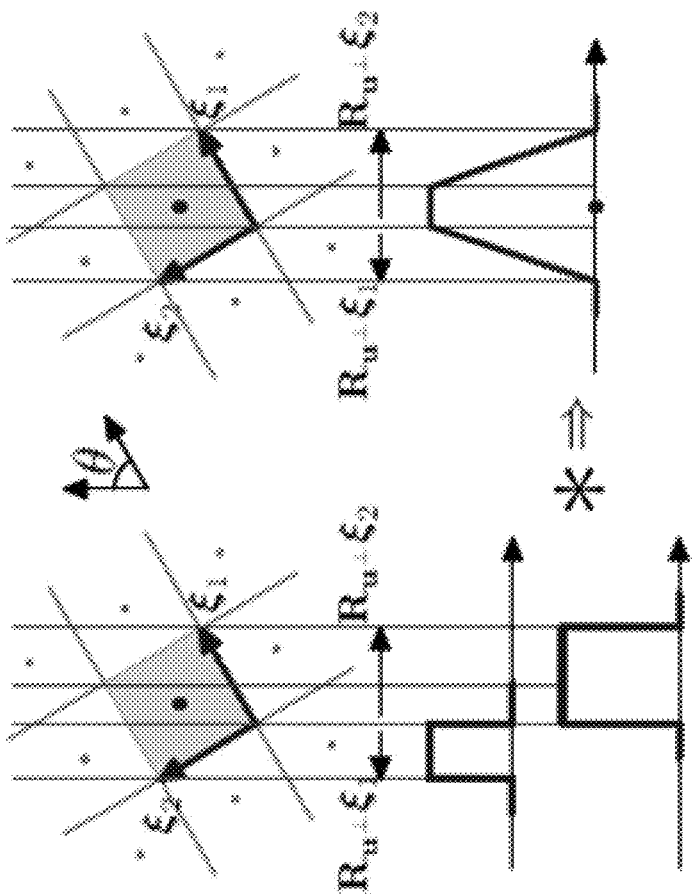
Figure 8:
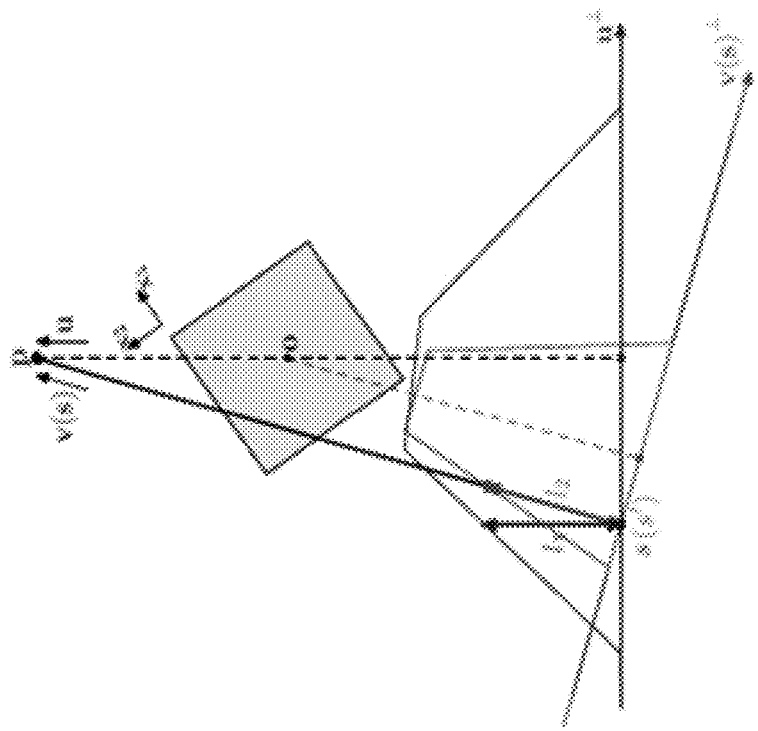
Figure 9:
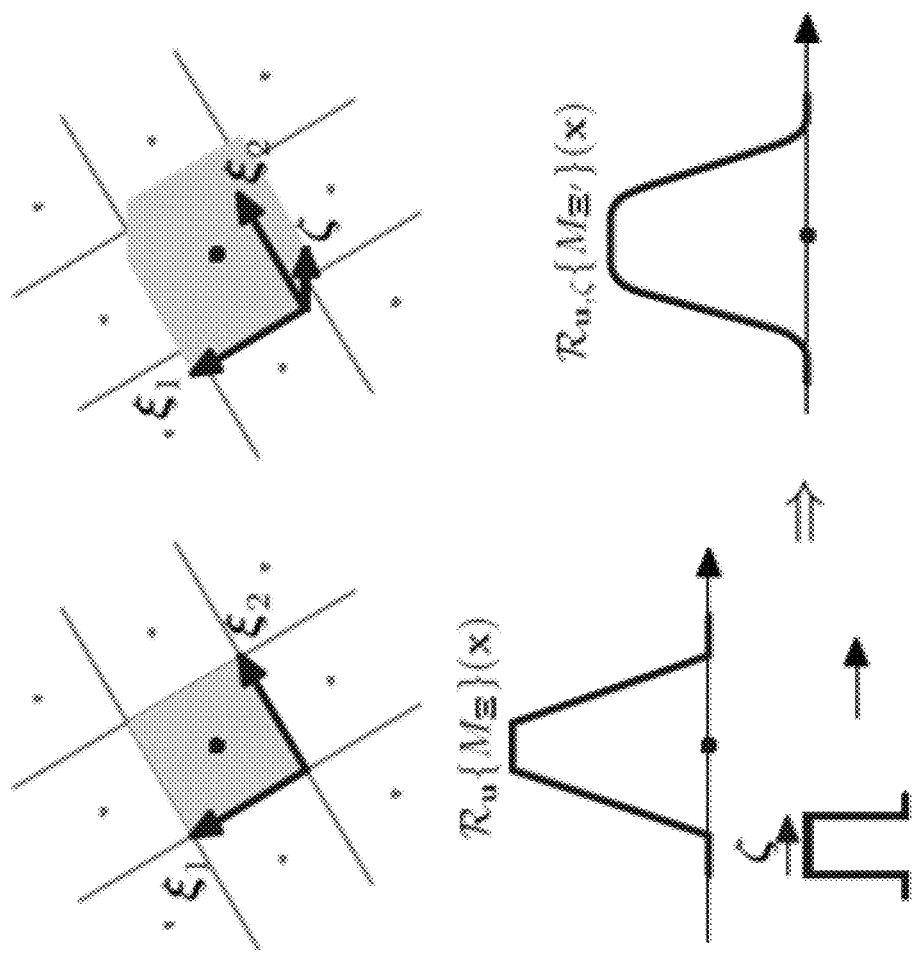
Figure 10:
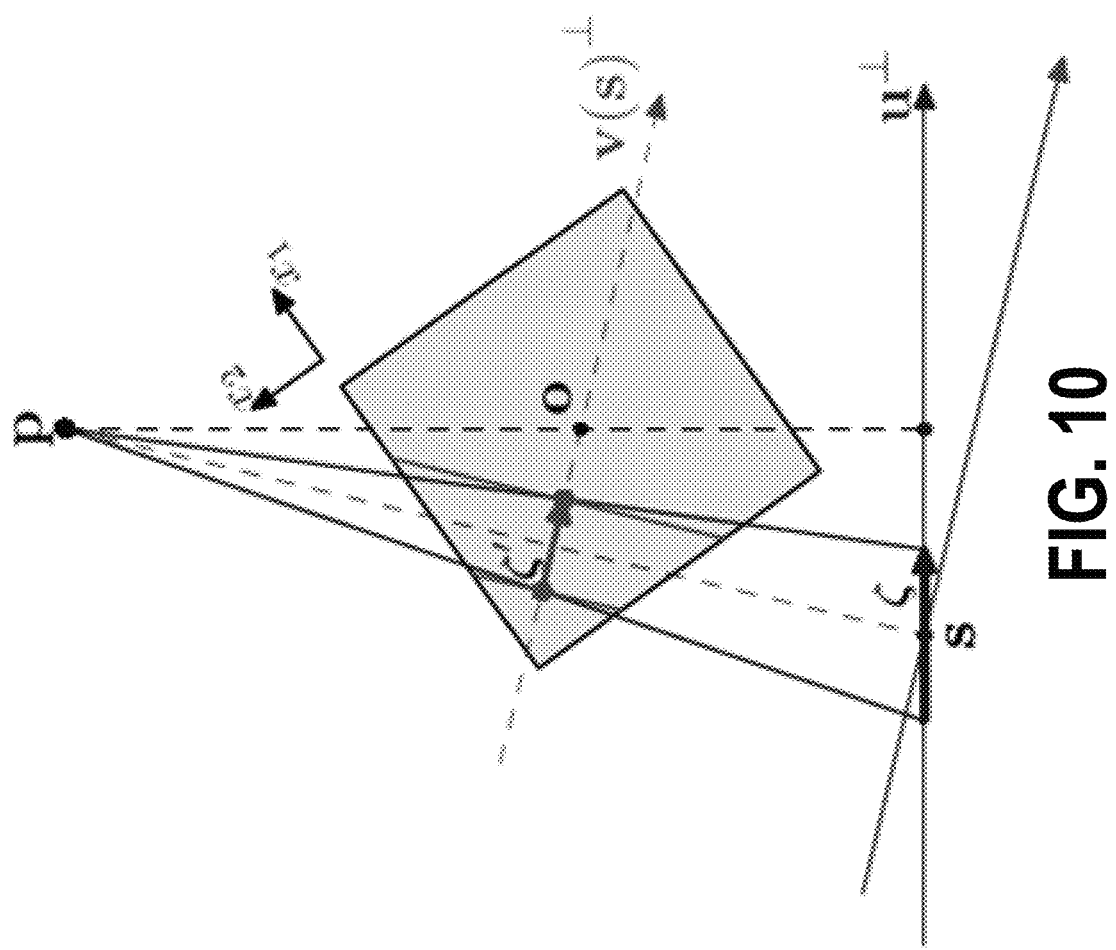
Figure 11:
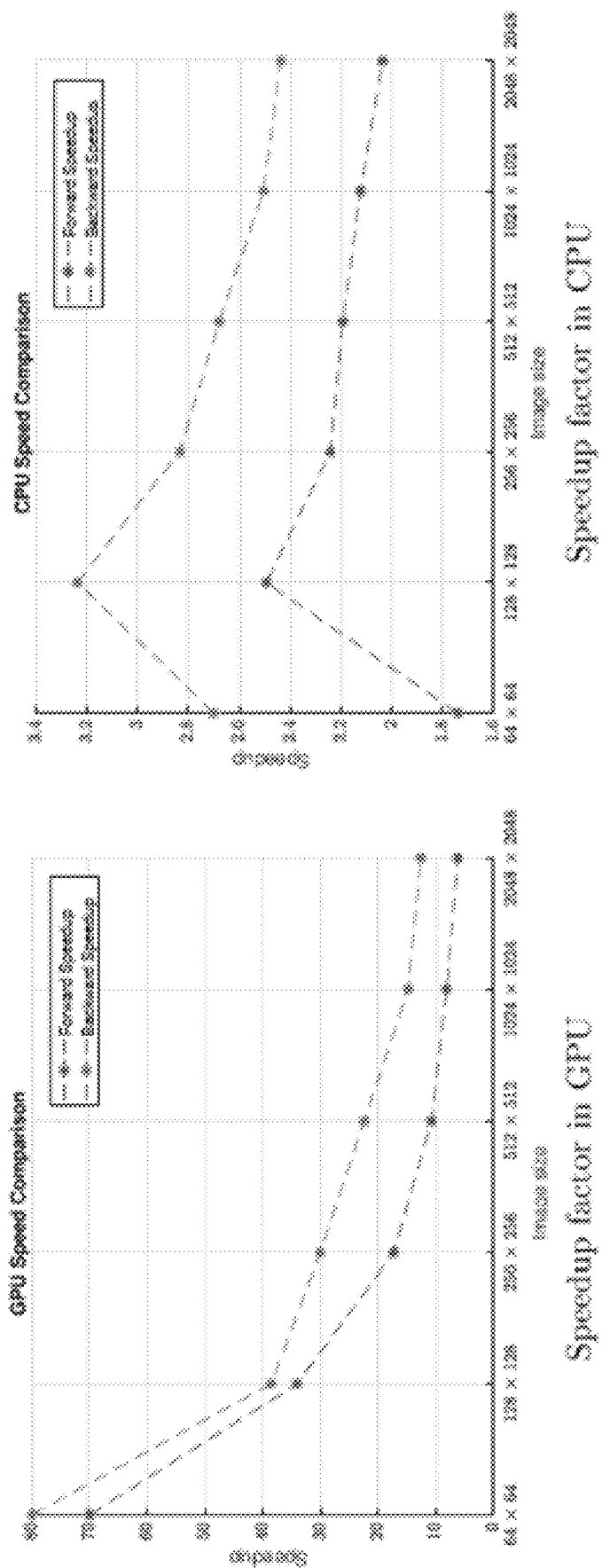
Figure 12:
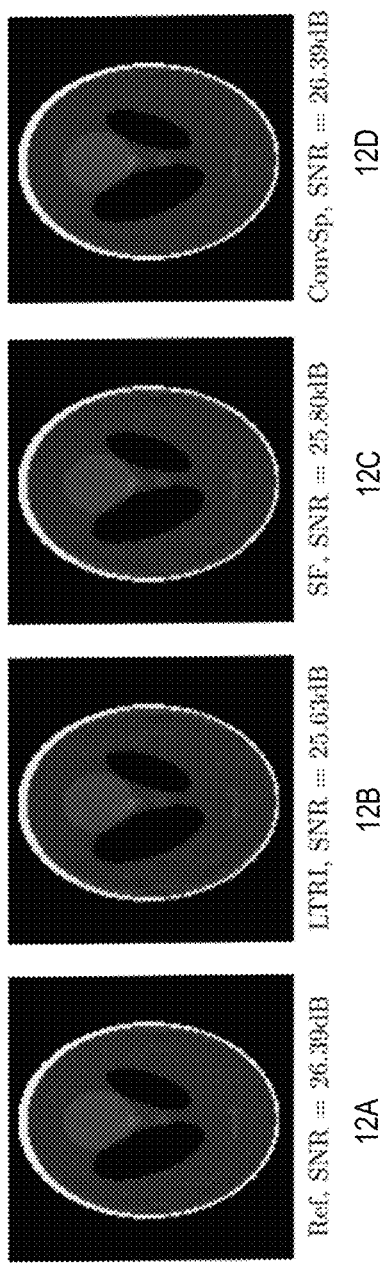
Figure 13:
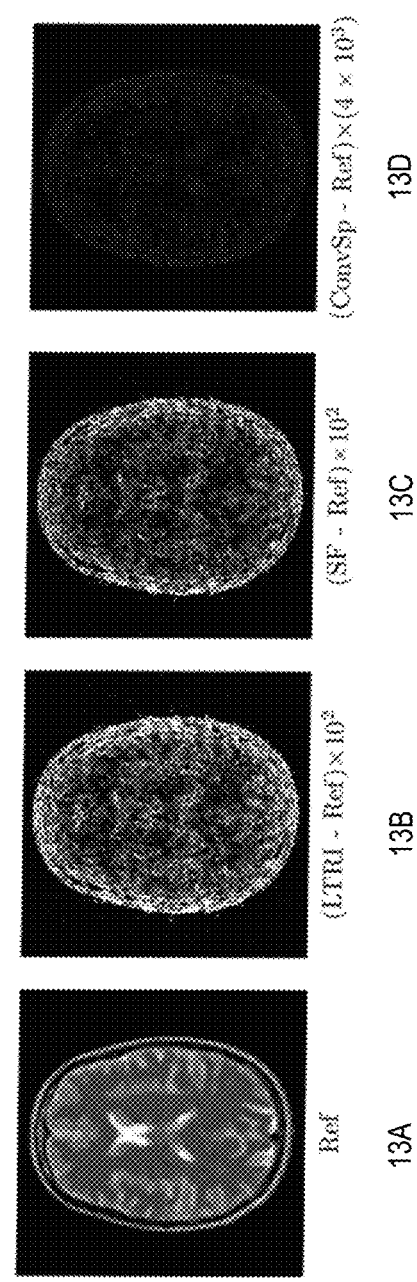
Figure 14:
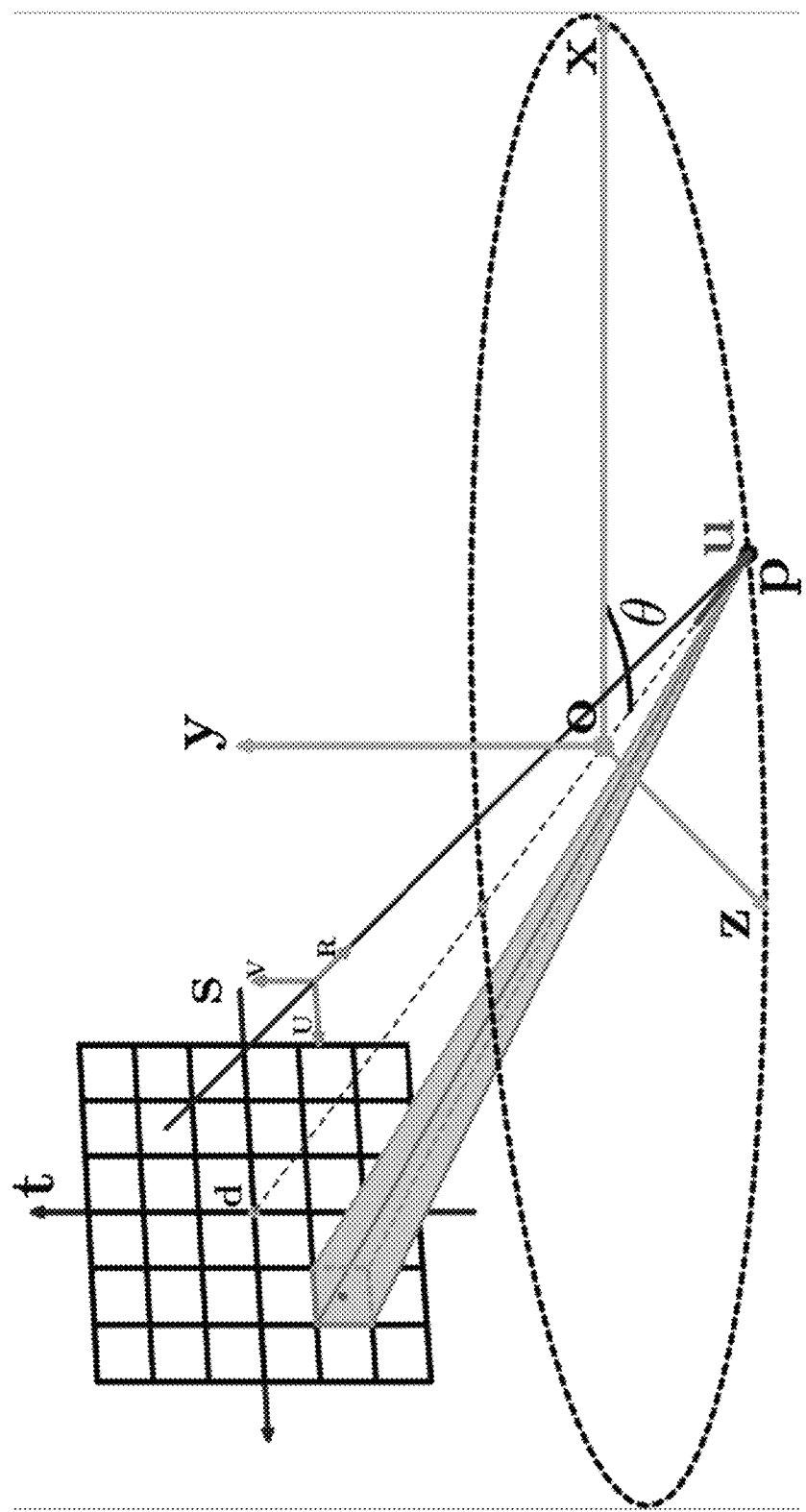
Figure 15:
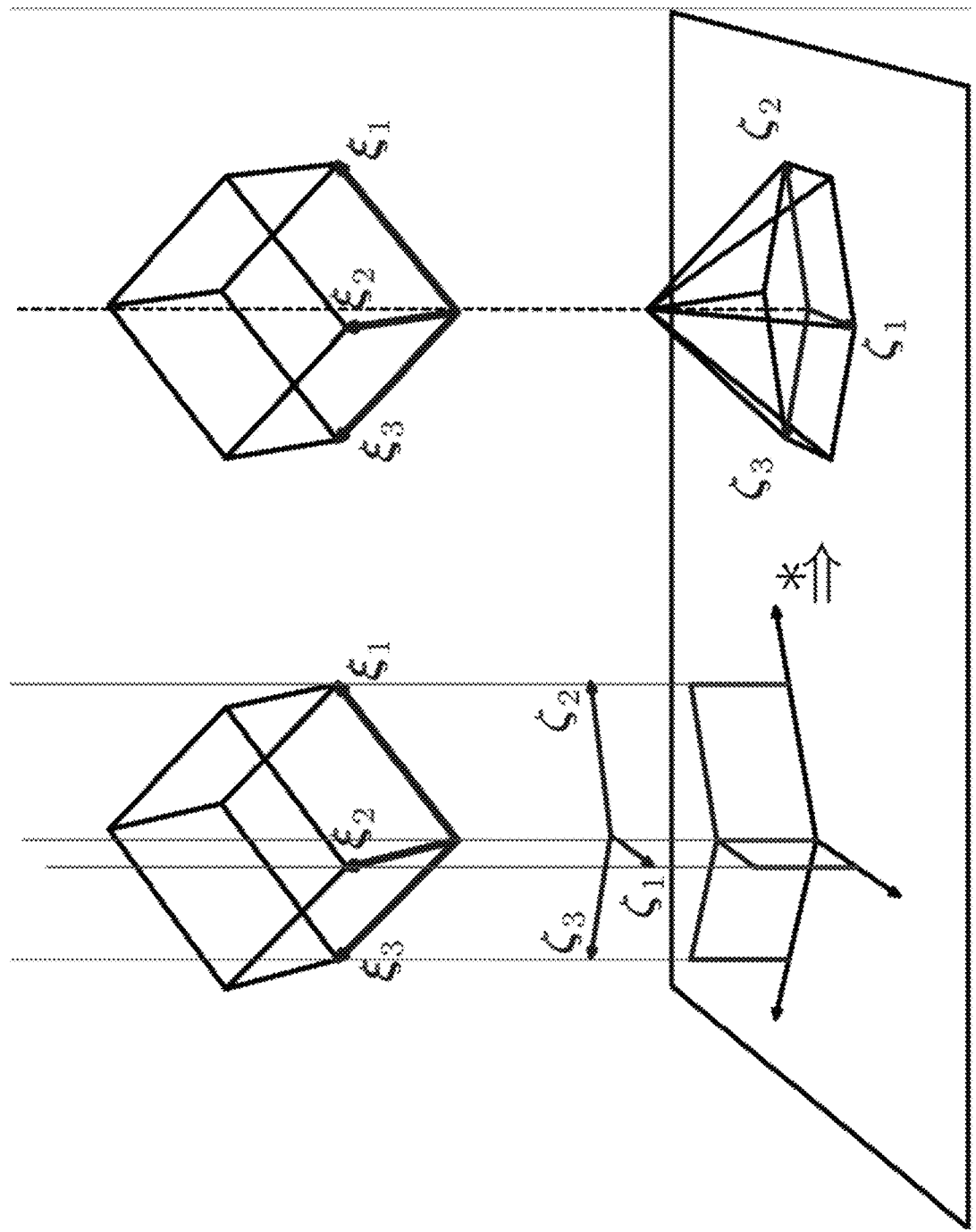
Figure 16:
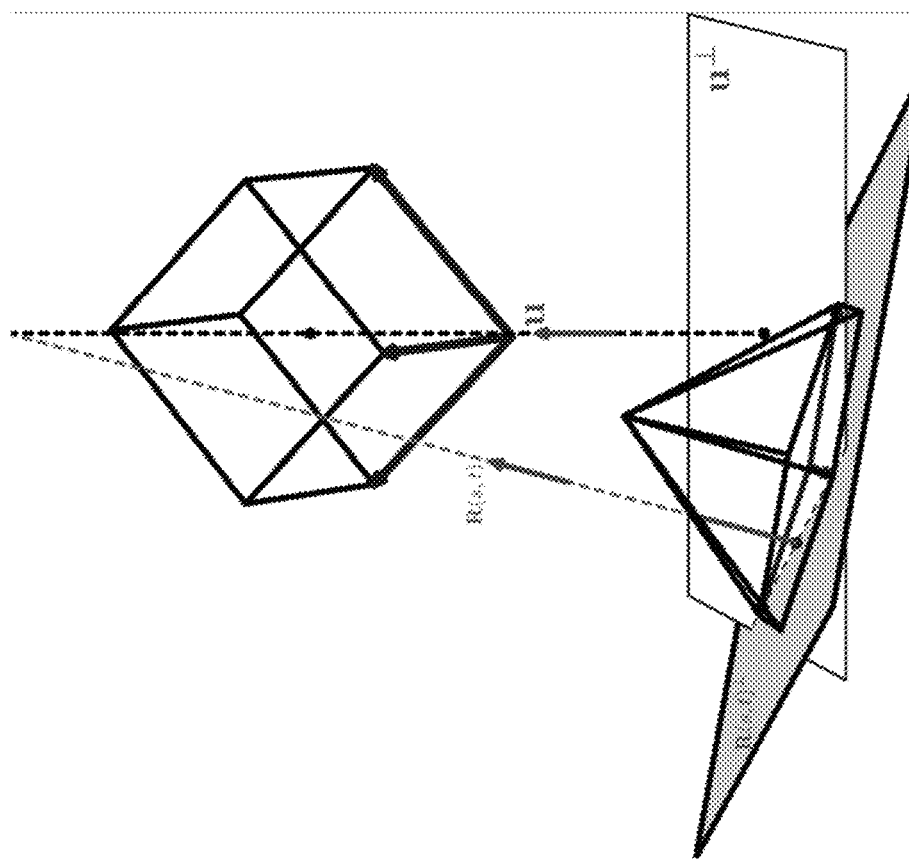
Figure 17:
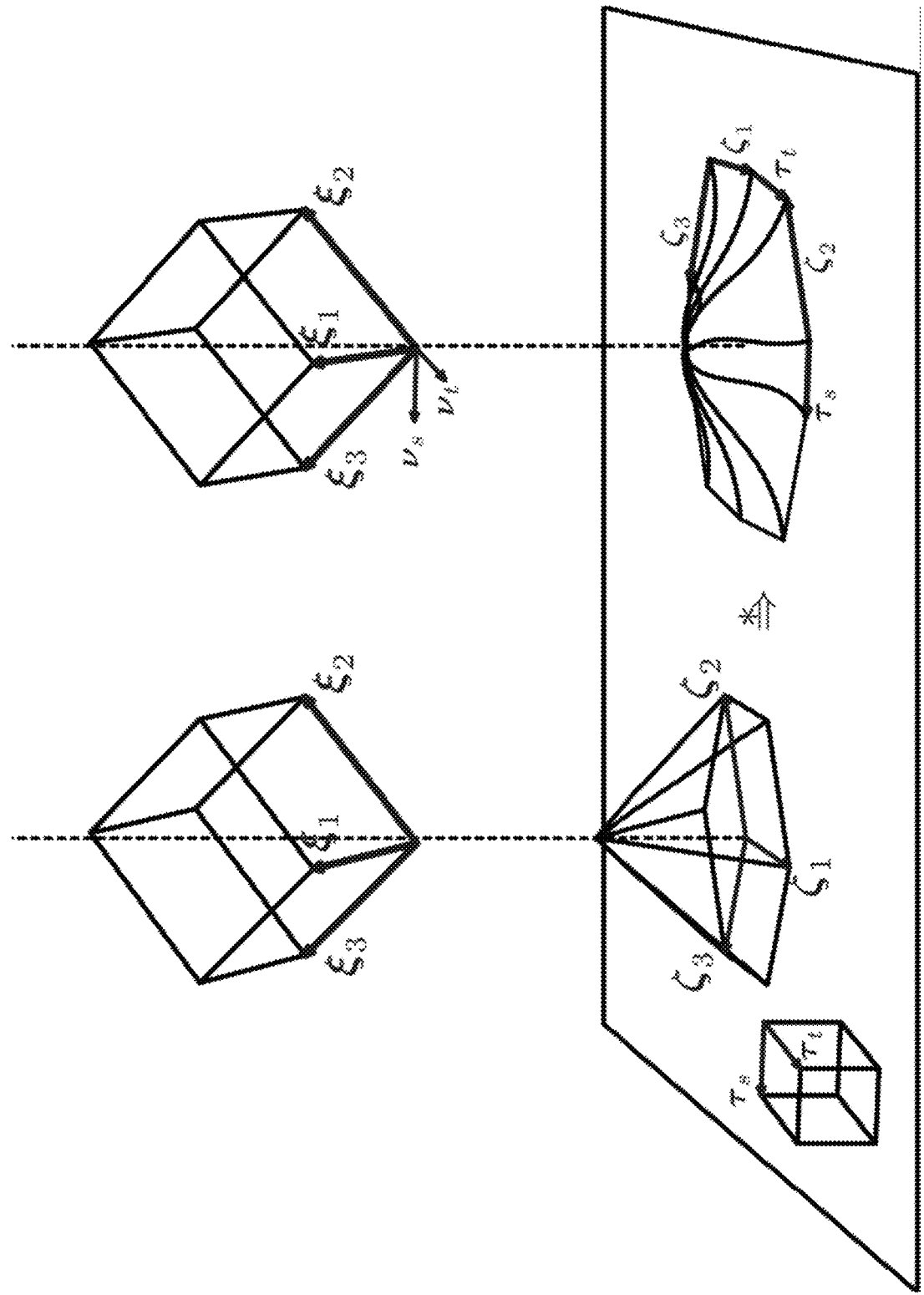
Figure 18:
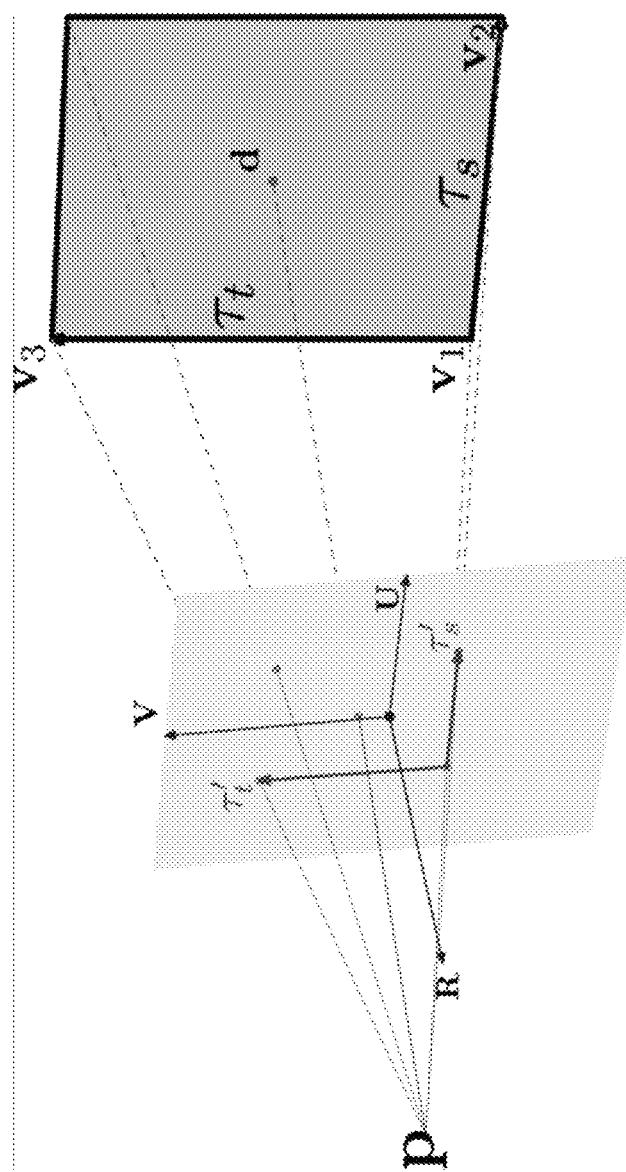
Figure 19:
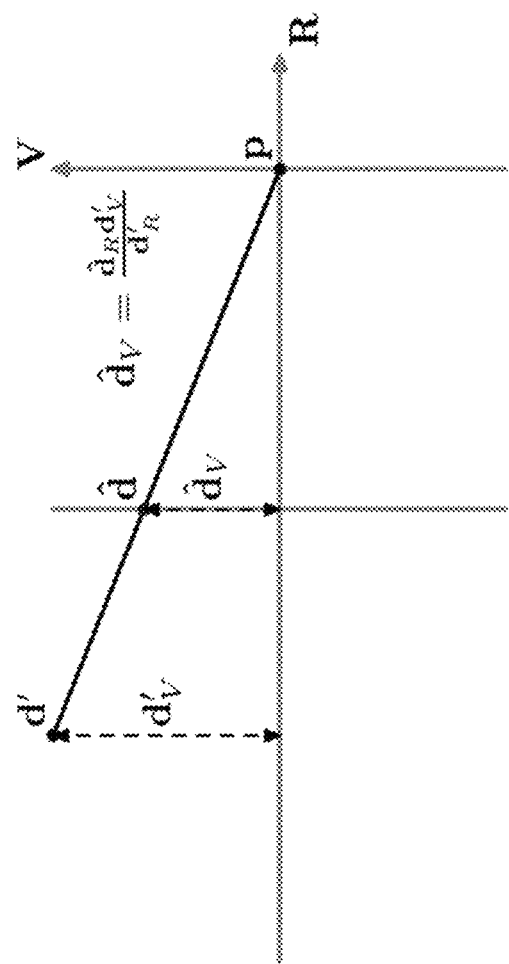

Having thus described the invention in general terms, reference will now be made to the accompanying drawings, which are not necessarily drawn to scale, and wherein:

FIG. 1 illustrates an example fan-beam geometry used in an example embodiment of the present invention;

FIG. 2 is an overview of a system that can be used to practice embodiments of the present invention;

FIG. 3 is an exemplary schematic diagram of an image reconstruction computing entity according to one embodiment of the present invention;

FIG. 4 is an exemplary schematic diagram of a user computing entity according to one embodiment of the present invention;

FIG. 5 provides a flowchart illustrating example processes, procedures, and/or operations for determining an individual's parkinsonian state;

FIG. 6 illustrates, from left to right, that the Box Splines can be constructed by convolving elementary Box Splines in specific directions;

FIG. 7 provides an illustration of a projection of the pixel basis as a convolution;

FIG. 8 provides an illustration of an 1-D point-wise box spline;

FIG. 9 provides an illustration of the projection of a 2-D box spline with detector blur in a parallel-beam, in accordance with an example embodiment;

FIG. 10 provides an illustration of the projection of a box spline with effective detector blur in a fan-beam geometry, in accordance with an example embodiment;

FIG. 11 provides graphs showing the speedup (e.g., factor of reduction in time) for reconstructing the image in GPU and CPU implementations compared to SF and LTRI image reconstruction techniques measured in various resolutions relevant to clinical image reconstructions settings (in GPU computations, a factor of at least 20 speedup and in CPU computations a factor of at least 2-3 speedup has been observed in 2-D fan-beam geometry);

FIG. 12 illustrates the reconstruction of the Shepp-Logan phantom using various methods, including the forward and back method of the present invention; and FIG. 13 illustrates a reference projector reconstruction of the brain phantom and the difference between the reference projector reconstruction and three other reconstruction methods, including the forward and back method of the present invention;

FIG. 14 illustrates an example cone-beam geometry used in an example embodiment of the present invention;

FIG. 15 provides an illustration of a projection of the voxel basis as a convolution;

FIG. 16 provides an illustration of a 2-D point-wise box spline;

FIG. 17 provides an illustration of the projection of a 3-D box spline with detector blur in a parallel-beam, in accordance with an example embodiment;

FIG. 18 provides an illustration of the example of effective detector blur in a cone-beam geometry;

FIG. 19 provides an illustration of the 2-D view of perspective projection.

DETAILED DESCRIPTION OF SOME EXAMPLE EMBODIMENTS

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

Various embodiments provide methods, systems, apparatus, computer program products and/or the like for provides reconstructing and/or generating an image based on projection information/data using a forward and back projection technique that employs a convolutional spline process. The convolution spline process comprises using a box spline basis set for a footprint and/or detector blur computation used to generate and/or reconstruct the image. The projection information/data is captured by an imaging device via an imaging process such as X-ray CT, PET, SPECT, and/or the like. The projection information/data is captured using a low-dose, few view, and/or limited view technique that reduces the amount of radiation experienced by the individual (e.g., patient, study participant, and/or the like) being imaged. The image is provided to a user computing entity such that the user computing entity may display the image via a user interface thereof. In various embodiments, the image is provided within ten minutes of the projection information/data being received by the image reconstruction computing entity. Various embodiments provided a faster and more accurate image generation and/or reconstruction than methods known in the art (e.g., separable footprint (SF), look-up table-based ray integration (LTRI)). Various embodiments may be used to reconstruct and/or generate images based on projection information/data captured by imaging devices having flat (e.g., planar) and/or arc (e.g., curved) detectors.

The forward and back projection technique uses a convolution spline process to provide the improved image reconstruction and/or generation based on the projection information/data. In particular, the convolutional spline process uses a box spline basis set for a footprint and/or detector blur computation used to generate and/or reconstruct the image. In various embodiments, a fan-beam geometry is defined. FIG. 1 illustrates an example 2D fan-beam geometry. In various embodiments, 1D, 2D, fan-beam and/or 3D cone-beam geometries may be used. To specify the fan-beam geometry illustrated in FIG. 1, point p denotes the location of the projector, point d indicates the center of the detector plane, and vector u points from the center of the detector plane (e.g., point d) to the projector (e.g., point p). A point that acts as the rotation center (and/or origin) in the plane of the geometry (e.g., $\mathbb{R}^2$) is denoted o. A hyperplane $u^\perp$ orthogonal to the direction denotes the detector plane and point d is the center of the detector plane $u^\perp$. The collection or set of points s illustrates the collection of footprints of the rays emitted by the projector at point p on the detector plane $u^\perp$. Footprint $s_i$ illustrates the footprint of ray $r_i$ emitted by the projector on the detector plane $u^\perp$. The coordinates $x_1$ and $x_2$ define an orthogonal coordinate system that may be rotated around the center of rotation (e.g., origin) o to by an angle θ to provide an orthogonal coordinate system that may be used for efficient and highly accurate calculation and/or determination of the footprint $s_i$ of ray $r_i$ using the box spline basis set. FIG. 14 illustrates the cone-beam geometry. The source p rotated around a circle trajectory of radius $D_{src}$, which can be parameterized as:

$$p = D_{so} \begin{bmatrix} \cos\theta \\ 0 \\ \sin\theta \end{bmatrix}$$

where θ is the projection angle of source clockwise from x-axis. Let's u denote the unit vector from rotation center to source, and 2-D detector plane represented by the local coordinates (s,t) is perpendicular to u, where the s-axis is perpendicular to y-axis and t-axis is parallel to y-axis.

Together with u, these three axes can form a new coordinate system represented by the basis matrix:

$$B_p = \begin{bmatrix} \cos\theta & 0 & -\sin\theta \\ 0 & 1 & 0 \\ \sin\theta & 0 & \cos\theta \end{bmatrix}$$

or simplicity we name this source-detector frame as PTS frame. Let $v \in \mathbb{R}^3$ be the spatial coordinates of the input function (image domain), so it can be parameterized as: $v = p + \Delta r(s,t)$, where $\Delta$ is the parameter, and $r(s,t)$ is the unit direction of each X-ray, which can be computed by:

$$r(s, t) = \text{normalize}(B_p) \begin{bmatrix} D_{sd} \\ t \\ s \end{bmatrix},$$

where $D_{sd}$ is the distance from source to detector plane, and the operator normalize is simply to make the length of the vector equal to 1.

I. Computer Program Products, Methods, and Computing Entities

Embodiments of the present invention may be implemented in various ways, including as computer program products that comprise articles of manufacture. A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. Exemplary System Architecture

FIG. 2 provides an illustration of an exemplary embodiment of the present invention. As shown in FIG. 2, this particular embodiment may include one or more imaging machines/devices 115, one or more image reconstruction entities 100, one or more networks 105, and one or more user computing entities 110. Each of these components, entities, devices, systems, and similar words used herein interchangeably may be in direct or indirect communication with, for example, one another over the same or different wired or wireless networks. Additionally, while FIG. 2 illustrates the various system entities as separate, standalone entities, the various embodiments are not limited to this particular architecture.

1. Exemplary Image Reconstruction Computing Entity

FIG. 3 provides a schematic of an image reconstruction computing entity 100 according to one embodiment of the present invention. An image reconstruction computing entity 100 may belong to, a medical facility, hospital, clinic, diagnostic service, healthcare provider, healthcare provider group, and/or the like. However, the image reconstruction computing entity 100 may belong a third party computing service that performs remote computations for a medical facility. In an example embodiment, an image reconstruction computing entity 100 may be configured to control one or more imaging machines/devices 115 and/or to receive projection information/data from one or more imaging machines and/or a controller computing entity thereof. In various embodiments, an image reconstruction computing entity 100 is configured to process the projection information/data using a forward and back projection technique of the present invention to reconstruct an image corresponding to the projection information/data. In various embodiments, the image reconstruction computing entity is configured to provide (e.g., transmit) the image to a user computing entity 110 for provision and/or display via a display and/or other user interface thereof.

In general, the terms computing entity, computer, entity, device, system, and/or similar words used herein interchangeably may refer to, for example, one or more computers, computing entities, desktop computers, mobile phones, tablets, phablets, notebooks, laptops, distributed systems, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the image reconstruction computing entity 100 may also include one or more communications interfaces 220 for communicating with various computing entities, such as by communicating data, content, information, and/or similar terms used herein interchangeably that can be transmitted, received, operated on, processed, displayed, stored, and/or the like. For instance, the image reconstruction computing entity 100 may communicate with user computing entities 110 and/or a variety of other computing entities.

As shown in FIG. 3, in one embodiment, the image reconstruction computing entity 100 may include or be in communication with one or more processing elements 205 (also referred to as processors, processing circuitry, and/or similar terms used herein interchangeably) that communicate with other elements within the image reconstruction computing entity 100 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly. In various embodiments, the processing elements 205 comprise one or more graphical processing units (GPUs).

In one embodiment, the image reconstruction computing entity 100 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the image reconstruction computing entity 100 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the image reconstruction computing entity 100 with the assistance of the processing element 205 and operating system.

As indicated, in one embodiment, the image reconstruction computing entity 100 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the image reconstruction computing entity 100 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra wideband (UWB), infrared (IR) protocols, near field communication (NFC) protocols, Wibree, Bluetooth protocols, wireless universal serial bus (USB) protocols, and/or any other wireless protocol.

Although not shown, the image reconstruction computing entity 100 may include or be in communication with one or more input elements, such as a keyboard input, a mouse input, a touch screen/display input, motion input, movement input, audio input, pointing device input, joystick input, keypad input, and/or the like. The image reconstruction computing entity 100 may also include or be in communication with one or more output elements (not shown), such as audio output, video output, screen/display output, motion output, movement output, and/or the like.

In various embodiments, the image reconstruction computing entity 100 may further comprise a user interface for user interaction. In various embodiments, the user interface may comprise one or more input devices (e.g., soft or hard keyboard, joystick, mouse, touch screen device, microphone, and/or the like) for receiving user input and one or more output devices (e.g., speakers, display, and/or the like) for providing output to a user.

As will be appreciated, one or more of the image reconstruction computing entity's 100 components may be located remotely from other image reconstruction computing entity 100 components, such as in a distributed system. Furthermore, one or more of the components may be combined and additional components performing functions described herein may be included in the image reconstruction computing entity 100. Thus, the image reconstruction computing entity 100 can be adapted to accommodate a variety of needs and circumstances. As will be recognized, these architectures and descriptions are provided for exemplary purposes only and are not limiting to the various embodiments.

2. Exemplary User Computing Entity

A user may be an individual, a family, a company, an organization, an entity, a department within an organization, a representative of an organization and/or person, and/or the like. In one example, users may be medical personnel, doctors, physician assistants, nurses, patients, and/or the like. For instance, a user may operate a user computing entity 110 that includes one or more components that are functionally similar to those of the image reconstruction computing entity 100. For example, a user computing entity 110 may be configured to receive an image (e.g., generated and/or provided by an image reconstruction computing entity 100) and provide and/or display the image (e.g., via a display, screen, monitor, and/or the like). FIG. 4 provides an illustrative schematic representative of a user computing entity 110 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, wearables, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. User computing entities 110 can be operated by various parties. As shown in FIG. 4, the user computing entity 110 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, respectively.

The signals provided to and received from the transmitter 304 and the receiver 306, respectively, may include signaling information in accordance with air interface standards of applicable wireless systems. In this regard, the user computing entity 110 may be capable of operating with one or more air interface standards, communication protocols, modulation types, and access types. More particularly, the user computing entity 110 may operate in accordance with any of a number of wireless communication standards and protocols, such as those described above with regard to the image reconstruction computing entity 100. In a particular embodiment, the user computing entity 110 may operate in accordance with multiple wireless communication standards and protocols, such as UMTS, CDMA2000, 1×RTT, WCDMA, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the user computing entity 110 may operate in accordance with multiple wired communication standards and protocols, such as those described above with regard to the image reconstruction computing entity 100 via a network interface 320.

Via these communication standards and protocols, the user computing entity 110 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 110 can also download changes, add-ons, and updates, for instance, to its firmware, software (e.g., including executable instructions, applications, program modules), and operating system.

According to one embodiment, the user computing entity 110 may include location determining aspects, devices, modules, functionalities, and/or similar words used herein interchangeably. For example, the user computing entity 110 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites. The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. Alternatively, the location information can be determined by triangulating the user computing entity's 110 position in connection with a variety of other systems, including cellular towers, Wi-Fi access points, and/or the like. Similarly, the user computing entity 110 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The user computing entity 110 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the user computing entity 110 to interact with and/or cause display of information from the image reconstruction computing entity 100, as described herein. The user input interface can comprise any of a number of devices or interfaces allowing the user computing entity 110 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the user computing entity 110 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The user computing entity 110 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the user computing entity 110. As indicated, this may include a user application that is resident on the entity or accessible through a browser or other user interface for communicating with the image reconstruction computing entity 100 and/or various other computing entities.

In another embodiment, the user computing entity 110 may include one or more components or functionality that are the same or similar to those of the image reconstruction computing entity 100, as described in greater detail above. As will be recognized, these architectures and descriptions are provided for exemplary purposes only and are not limiting to the various embodiments.

3. Exemplary Imaging Machine

In various embodiments, an imaging machine/device 115 may be an imaging machine configured to capture and/or generate projection information/data used to create a 2D or 3D image of a portion of an individual's (e.g., patient, study participant, and/or the like) body. In various embodiments, the imaging machine/device 115 is configured for capturing and/or generating projection information/data through at least one of the various imaging techniques and/or processes such as, for example, X-ray CT, PET, SPECT.

In an example embodiment, the imaging machine/device 115 may be operated by the image reconstruction computing entity 100 and/or other controller computing entity. In an example embodiment, the imaging machine and/or controller computing entity thereof may communicate with the image reconstruction computing entity 100 directly and/or via one or more wired and/or wireless networks 105. For example, the imaging machine/device 115 may be configured to provide projection information/data to the image reconstruction computing entity 100 for analysis, storage, and/or the like. In another example, the image reconstruction computing entity 100 and/or other controller computing entity may provide instructions to the imaging machine/device 115 regarding beginning an imaging session, pausing an imaging session, aborting an imaging session, ending an imaging session, and/or the like.

III. Exemplary System Operation

According to various embodiments, the image reconstruction computing entity 100 may be configured to analyze one or more instances of projection information/data and reconstruct one or more images from the instance(s) projection information/data. In various embodiments, the image is reconstructed from the projection information/data using a forward and back projection technique. In an example embodiment, an instance of projection information/data may comprise the projection information/data of one imaging session and/or a portion of one imaging session, for one individual (e.g., patient, study participant, and/or the like). The term "image" is used generically to refer to a variety of images that can be generated from various imaging techniques and processes. The imaging techniques and processes may include, for instance, X-ray CT, PET, SPECT, and/or the like. As indicated, the images can be of a human body or one or more parts of the human body (e.g., a patient and/or study participant's brain), but the images can also be of other organisms or objects.

In various embodiments, the forward and back projection technique may be used to reconstruct the image from the projection information/data in a reasonable time period for clinical settings. For example, an example embodiment reconstructs the image from the projection information/data in less than ten minutes. In various embodiments, the forward and back projection technique is performed using a convolutional spline process and/or basis set. For example, in various embodiments, the forward and back projection technique employs the convolution properties of splines to perform accurate footprint and detector blur computations in a computationally efficient and fast manner.

In various embodiments, the reconstructed image is provided (e.g., transmitted) by the image reconstruction computing entity 100 such that a user computing entity 110 receives the image. The user computing entity 110 may process the image and cause a display, screen, monitor, or other user interface to display the image.

FIG. 5 provides a flowchart illustrating various process, procedures, operations, and/or the like for generating and providing an image, in accordance with an example embodiment. Starting at step/operation 402, projection information/data is captured. For example, the image reconstruction computing entity 100 may receive from or cause an imaging machine/device 115 to capture projection information/data of an individual. For example, an imaging technician may provide the individual with instructions and position the individual within and/or in the proximity of the imaging machine/device 115. The imaging technician may then provide input (e.g., via a user input device) to the image reconstruction computing entity 100 to trigger the image reconstruction computing entity 100 to cause, instruct, trigger, and/or the like the imaging machine/device 115 to capture projection information/data of the individual. The image reconstruction computing entity 100 may receive the captured projection information/data from the imaging machine/device 115 and store the projection information/data and corresponding metadata in memory 210, 215. For example, the metadata may include the individual's name or an individual identifier, a date and/or time stamp, information/data identifying the imaging machine/device 115, and/or the like. In an example embodiment, the projection information/data captured may comprise X-ray CT, PET, SPECT, and/or other projection information/data. In various embodiments, the projection information/data is captured (by the imaging machine/device 115) using a low-dose, few view, and/or limited view technique. In various embodiments, the projection information/data may comprise one or more images of an individual's body, brain, other body part, and/or a portion thereof.

At step/operation 404, the projection information/data is processed and an image is reconstructed based at least in part on the projection information/data. In various embodiments, the image is reconstructed from the projection information/data using a forward and back projection technique. In various embodiments, the forward and back projection technique is performed using a convolutional spline process and/or basis set. For example, in various embodiments, the forward and back projection technique employs the convolutional properties of splines to efficiently and accurately reconstruct an image from the projection information/data. For example, the image reconstruction computing entity 100 may use a forward and back projection technique to reconstruct the image from the projection information/data.

In various embodiments, reconstructing the image from the projection information/data comprises performing footprint and detector blur computations. U.S. Pat. No. 8,913,805, the content of which is hereby incorporated in its entirety by reference, provides an example of footprint and detector blur computations. However, in a marked difference from U.S. Pat. No. 8,913,805, various embodiments of the present invention employ a convolutional spline process and/or basis for performing the footprint and detector blur computations. This choice of basis leads to a significant improvement in the speed and accuracy with which the footprint and detector blur computations are performed such that the resulting image may be reconstructed in a highly computationally efficient manner and may be highly accurate.

Box Splines are smooth piecewise polynomial functions, generalizing B-splines (basic splines) to multi-dimensions, that are formed from projection of a hypercube in $\mathbb{R}^N$ to $\mathbb{R}^d$. The simplest box spline can be constructed in $\mathbb{R}^d$ as the indicator function of the d-dimensional hypercube (identity projection) that is the pixel- and voxel-basis function when d=2 and 3. They also have a convolutional construction that plays a role in the following derivation of footprint and detector blur.

In d-dimension, $d \geq 1$, an elementary box spline, $M_\xi$, associated with a vector $\xi$ in $\mathbb{R}^d$ can be thought of as the indicator function of the set $\{t\xi | 0 \leq t \leq 1\}$ and is defined as a Dirac-line distribution (generalized function) defined by its action on a function $f(x)$ in $\mathbb{R}^d := \int_0^1 f(x-t\xi)dt$. Given a set of directions, arranged in columns, as $\Xi := [\xi_1, \xi_2, \ldots, \xi_N]$, the general box spline can be constructed by: $M_\Xi(x) = (M_{\xi_1} * M_{\xi_2} * \ldots * M_{\xi_N})(x)$, as illustrated in FIG. 6. When the directions are orthogonal in special, $M_\Xi$ is a tensor-product B-spline with the repeats of a direction elevating the degree of the B-spline.

Key to this innovation is our unique method for computing (evaluating) 1-d and 2-d box splines very efficiently and stably in multi-directions. The 2 directional univariate (1-d) box spline can be evaluated as:

$$M_\Xi(x) = M_{[\xi_1, \xi_2]}(x) = \min\left(\max\left(\frac{\frac{|\xi_1| + |\xi_2|}{2} - |x|}{2}, 0\right), \max(|\xi_1|, |\xi_2|)\right). \quad (1)$$

The 3 directional univariate box spline is a quadratic piecewise polynomial that is evaluated by:

$M_\Xi(x) =$  (2)

$$M_{[\xi_1,\xi_2,\xi_3]}(x) = \begin{cases} \dfrac{\left(\dfrac{\xi_1+\xi_2+\xi_3}{2}-|x|\right)^2}{2|\xi_1\xi_2\xi_3|}, & \dfrac{\xi_1-\xi_2+\xi_3}{2} \leq |x| < \dfrac{\xi_1+\xi_2+\xi_3}{2} \\[1em] \dfrac{\xi_1+\xi_2}{(2-|x|)|\xi_1\xi_2|}, & \dfrac{\xi_1+\xi_2-\xi_3}{2} \leq |x| < \dfrac{\xi_1-\xi_2+\xi_3}{2} \\[1em] \dfrac{1}{\max(|\xi_1|,|\xi_2|,|\xi_3|)} - \dfrac{\left(\dfrac{\xi_1-\xi_2-\xi_3}{2}-|x|\right)^2}{2|\xi_1\xi_2\xi_3|}, & \left|\dfrac{\xi_1-\xi_2-\xi_3}{2}\right| \leq |x| < \dfrac{\xi_1+\xi_2-\xi_3}{2} \\[1em] \dfrac{1}{\max(|\xi_1|,|\xi_2|,|\xi_3|)}, & |x| < \left|\dfrac{\xi_1-\xi_2-\xi_3}{2}\right| \text{ and } \dfrac{\xi_1-\xi_2-\xi_3}{2} > 0 \\[1em] \dfrac{1}{\max(|\xi_1|,|\xi_2|,|\xi_3|)} - \dfrac{\left(\dfrac{\xi_1-\xi_2-\xi_3}{2}\right)^2+x^2}{2|\xi_1\xi_2\xi_3|}, & |x| < \left|\dfrac{\xi_1-\xi_2-\xi_3}{2}\right| \text{ and } \dfrac{\xi_1-\xi_2-\xi_3}{2} < 0, \end{cases}$$

where $\xi_1, \xi_2, \xi_3$ are sorted in descending order after taking their absolute values. This sorting of their absolute value guarantees the order of the intervals. In addition, the 3 directional bivariate (2-d) box spline can be evaluated by:

$v_1 = \langle \xi_1^\perp, \xi_2 \rangle, v_2 = \langle \xi_1^\perp, \xi_3 \rangle, v_3 = \langle \xi_2^\perp, \xi_3 \rangle;$ $u_1 = \langle \xi_1^\perp, x \rangle, u_2 = \langle \xi_2^\perp, x \rangle, u_3 = \langle \xi_3^\perp, x \rangle;$ $d_1 = \dfrac{|v_1|+|v_2|}{2} - \left|\dfrac{u_1 - \dfrac{(v_1+v_2)}{2}}{v_1 v_2}\right|, -d_2 = \dfrac{|v_1|+|v_3|}{2} - \left|\dfrac{u_1 - \dfrac{(v_1+v_3)}{2}}{v_1 v_3}\right|,$ $d_3 = \dfrac{|v_2|+|v_3|}{2} - \left|\dfrac{u_1 - \dfrac{(v_2+v_3)}{2}}{v_2 v_3}\right|;$ $h = \dfrac{1}{\min(v_1, v_2, v_3)};$ $v = \max(0, \min(d_1, d_2 d_3, h));$ Return $v$;

In parallel-beam setting the projection (e.g., X-ray and Radon transforms) of a bivariate (2-d) box spline $M_\Xi(x)$ is a univariate (1-d) box spline, $M_{\Xi'}(y)$, in sinogram domain, where $\Xi'$ is the geometric projection of the directions in $\Xi$: $\Xi' := [R_u^\perp \xi_1, R_u^\perp \xi_2]$, where $\xi_1$ and $\xi_2$ are 2-d column vectors. Denoting $R_u$ as the map of a box spline from viewing direction specified by vector u in parallel-beam geometry, provides the result: $R_u\{M_\Xi\}(x) = M_{\Xi'}(y) = (M_{R_u^\perp \xi_1} * M_{R_u^\perp \xi_2})(y)$, where $R_u^\perp$ is the transformation matrix that geometrically projects the coordinates of the image domain onto a detector plane perpendicular to u, and an example of $R_u^\perp$ is $\begin{bmatrix} -\sin\theta \\ \cos\theta \end{bmatrix}^T$ where $\theta$ is the viewing angle. 3-D case requires the addition of the third direction: $\Xi' := [B_p^T \xi_1(2,3) B_p^T \xi_2(2,3), B_p^T \xi_3(2,$ 3)], where $\xi_1, \xi_2$ and $\xi_3$ are 3-d column vectors and $b_p^t \xi_i(2,3)$ indicating reserving the last two components of the projected vector $B_p^T \xi_i$.

FIG. 7 shows a box spline in $R^2$ specified by directions $\Xi = [\xi_1, \xi_2]$ which coincides with a pixel-basis and, when projected to the sinogram domain, is a univariate box spline in R with two directions that is the convolution of two elementary box splines. In this example, the matrix $R_{u^\perp} = [\sin(\theta), -\cos(\theta)]$ specifies the direction of the projection plane, where $\theta$ is the viewing angle, and $\xi_1 = \begin{bmatrix} 1 \\ 0 \end{bmatrix}$ and $\xi_2 = \begin{bmatrix} 0 \\ 1 \end{bmatrix}.$ This formality may then be applied to determine the X-ray projection of a box spline in a fan beam. FIG. 15 shows the 3-D case.

In fan-beam geometry and cone-beam geometry, although the concept of X-ray and Radon transform of box splines still holds, the divergent nature of rays does not allow a direct application of that result. However, in fan-beam and cone-beam geometries, while rays are not perpendicular to the detector plane, orthogonal coordinate systems may be constructed for each individual ray by simple rotations of the detector plane and the projection for each individual ray may be evaluated in the corresponding orthogonal coordinate system by applying the theory in parallel-beam geometry. In such case, from one viewing angle, instead of a single box spline, a set of box splines are evaluated depending on the directions of rays. For example, the directions associated with the box spline vary with the projection point, therefore, the evaluation is one a set of box splines.

In order to explain the geometry, $P_{v(s)^\perp}^T$ denotes a matrix whose columns span the hyperplane $v(s)^\perp$ perpendicular to the direction of X-ray $v(s)$. The corresponding coordinate s' in the rotated coordinate system aligning with the ray will be: $s'=P_{v(s)^\perp} p$, where p is the position of the X-ray source. The 2D example is illustrated in FIG. 8. The integral or projection value of ray v(s) is represented by $\ell_1$. In the $u^\perp$ plane, it's difficult to evaluate the projection value of ray v(s) by using the box spline property, while it's straight forward to calculate the projection value of ray v(s) in the rotated plane $v(s)^\perp$. This allows for an exact determination of the footprint (e.g., projection value) of a ray in the corresponding rotated plane. The footprint represented by $\ell_2$ is effectively the same as $\ell_1$, as illustrated in FIG. 8.

As this principle of equal effect, the projection of box spline in fan-beam geometry can be accomplished exactly by application of equation $R_u\{M_\Xi\}(x)=M_{\Xi'}(x)=(M_{R_u^\perp \xi_1} * M_{R_u^\perp \xi_2})(x)$ and $s'=P_{v(s)^\perp}p$ and this yields: $P_u\{M_\Xi\}(s)=R_{v(s)}\{M_\Xi\}(s')=M_{\Xi'}(s')=R_{v(s)^\perp}\Xi(P_{v(s)^\perp}p)$. This is the non-parallel result corresponding to equation $$R_u\{M_\Xi\}(x) = M_{\Xi'}(x) = \left(M_{R_u^\perp \xi_1} * M_{R_u^\perp \xi_2}\right)(x)$$

for a general box spline Ξ. Unlike the parallel-beam, the directions associated with the box spline vary with the projection point, therefore, the evaluation is on a family of box splines. Similarly, this theory is suitable for 3-D case with slightly more complicated geometry. As illustrated in FIG. 14, the three orthogonal axes, R, U, V, constitute a virtual coordinate system. The R-axis is the inverse direction of the X-ray direction that can be computed in the PTS coordinate system as:

$$R = \begin{bmatrix} D_{sd} \\ -t \\ -s \end{bmatrix} / N_R,$$

where $N_R = \sqrt{D_{sd}^2 + t^2 + s^2}$ is the length of the ray. There are infinite many basis vectors in 3-D space orthogonal to R, for simpler computation, we can select one by setting one of the component to zero as $$U = \begin{bmatrix} -R_3 \\ 0 \\ R_1 \end{bmatrix} = \begin{bmatrix} s \\ 0 \\ D_{sd} \end{bmatrix} / N_U,$$

where $N_U = \sqrt{s^2 + D_{sd}^2}$ is the length of this selected vector. Then the last basis vector is the cross product of R and U such that $$V = R \otimes U = \begin{bmatrix} -\frac{td}{N_R N_U} \\ -\frac{N_U}{N_R} \end{bmatrix}.$$

Therefore, this virtual coordinate system can be represented by the basis matrix consisting of vectors of R, U, V (We notice that the vector R, U and V are related to s, t, R=R(s,t), so, for simplicity, we just omit the parameter (s,t). Since these three vectors are computed in the PTS frame, in order to represent them in image space, we need to left multiply the PTS basis $B_p$:

$$B_R = B_P[R, U, V]$$

$$= B_P \begin{bmatrix} d/N\_R & s/N\_U & -td/(N_R N_U) \\ -t/N\_R & 0 & -N_U/N_R \\ -s/N\_R & D_{sd}/N\_U & ts/(N_R N_U) \end{bmatrix}$$

With this virtual frame, we can derive the cone-beam result similar as fan-beam: $P_u\{M_\Xi\}(s,t)=M_{B_R^T\Xi(2,3)}(B_p^T(2,3))=M_{Z(s,t)}(u,v)$. The geometric explanation is illustrated in FIG. 16.

In a simple model of forward projection in fan-beam geometry or cone-beam geometry, one can do point-sampling on the projected basis function $M_{R_u^\perp \Xi}$ in the 1-D or 2-D sinogram domain: $R_{u,\zeta}\{M_\Xi\}(s)=\int \delta(s) R_u\{M_\Xi\}(x)dx$, or $R_{u,\tau}\{M_\Xi\}(s,t)=\int_s \delta(t) \int_s \delta(s) R_u\{M_\Xi\}(x)dx$, where ζ and τ=[τ_s, τ_t] are 1-D and 2-D blur width respectively, while in more realistic modeling of the transform model the projections are integrated across a detector cell with a finite bin width ζ in R such that this equation can be modified to $R_{u,\zeta}\{M_\Xi\}(s)=\int_{s-\zeta/2}^{s+\zeta/2} h_\zeta(s) R_\Xi\{M_\Xi\}(x)dx=R_u\{M_\Xi\}*h_\zeta(s)$, where h is the detector blur function and its support is bin width. Since the detectors are usually uniformly placed on the projection domain, the blur function is often modeled as a shift-invariant function. Because the detector sensitivity is often modeled as a constant function over the detector cell or with a drop-off at the cell boundary, the blur function can also be modeled as a box spline as the constant function in an elementary box spline so that $h_\zeta(s)=M_\zeta(s)$. By applying the convolutional construction of box spline, the convolution in the equation $R_{u,\zeta}\{M_\Xi\}(s)=\int_{s-\zeta/2}^{s+\zeta/2} h_\zeta(s) R_u\{M_\Xi\}(x) dx=R_u\{M_\Xi\}*h_\zeta(s)$ can be computed by a single evaluation of a box spline:

$$R_{u,\zeta}\{M_\Xi\}(s) = R_u\{M_\Xi\} * h_\zeta(s) = M_{[R_u^\perp \Xi, \zeta]}(s).$$

The other benefits from the box spline modeled detector blur function is that the detector width ζ is independent of position of detectors, therefore this convolutional spline framework allows any detector width without any limitation of distance between detector cells and is suitable for more general settings. In addition, the 3-D corresponding result can be extended from 2-D as: $R_{u,\tau}\{M_\Xi\}(s,t)=\int_{t-\tau_t/2}^{t+\tau_t/2} h_{\tau_t}(t) \int_{s-\tau_s/2}^{s+\tau_s/2} h_{\tau_s}(s) R_u\{M_\Xi\}(x)dx=R_u\{M_\Xi\}(x)**h_\tau(s,t)$.

As the detector cells lie on the detector plane, it's naturally perpendicular to the direction of projection. Hence, it indicates that the detector blur can be modeled in image space as a convolution of a basis function with an elementary box spline (see FIG. 9): $R_{u,\zeta}\{M_\Xi\}(s)=R_u\{M_{[\Xi,\zeta]}\}(s)$ or $R_{u,\tau}\{M_\Xi\}(s)=R_u\{M_{[\Xi,\tau]}\}(s)$ (see FIG. 17).

For fan-beam geometry, because of the non-parallel structure of rays, the convolution of the elementary box spline in the image domain does not hold. Nevertheless, an effective blur ζ', which intersects an area with pixel very close to the area interested by the detector source-bin triangle as illustrated in FIG. 10, is derived. To derive the ζ', the fact that ζ' is a perspective projection of ζ on the plane $v(s)^\perp$ is used.

Therefore, let's denote B (s) as the matrix whose columns are the basis vectors of the coordinate system built by $v(s)^\perp$ and (s), and $B_p$ is the perspective projection matrix. By utilizing the homogeneous transformation, we can achieve the $$\zeta' \text{ as: } \zeta' = \frac{\left(B_P B_{v(s)} P_{u^\perp}^T\left(s+\frac{\zeta}{2}\right)\right)x_1}{\left(B_P B_{v(s)} P_{u^\perp}^T\left(s+\frac{\zeta}{2}\right)\right)x_2} - \frac{\left(B_P B_{v(s)} P_{u^\perp}^T\left(s-\frac{\zeta}{2}\right)\right)x_1}{\left(B_P B_{v(s)} P_{u^\perp}^T\left(s-\frac{\zeta}{2}\right)\right)x_2}.$$

In this equation for $\zeta'$, due to the fact of perspective projection, the perspective division is needed after perspective transform, then the effective blur width $\zeta'$ can be achieved by differing the two projected coordinates. Analogically, in 3-D cone-beam, the effective blur width $\tau'=[\tau_s, \tau_t]$ is a parallelogram area surrounded and/or defined by the two vectors, $\tau_s'$, $\tau_t'$, which is the area cut by the cone-beam with the plane across the voxel center and perpendicular to the ray as illustrated in FIG. 18. Therefore, $\tau_s'$ and $\tau_t'$ are the perspective projection of $\tau_s$ and $\tau_t$ on U-V plane respectively. Let $v_1$, $v_2$ and $v_3$ as the three corner vertices of a detector cell, such that $v_2=v_1+\tau_t$ and $v_3=v_1+\tau_s$. The three coordinate can be transformed into RUV frame by left multiplication of transpose of the basis matrix $B_R$: $v_1'=B_R^T v_1$; $v_2'=B_R^T v\_2$; $v_3'=B_R^T v_3$. Then the perspective projection is achieved by performing the perspective division:

$$\tau_t' = \begin{bmatrix} (v_3'-v_1')_U \\ (v_3'-v_1')_V \end{bmatrix} / (v_3'-v_1')_R,$$

$$\tau_s' = \begin{bmatrix} (v_2'-v_1')_U \\ (v_2'-v_1')_V \end{bmatrix} / (v_2'-v_1')_R.$$

FIG. 9 illustrates the example of perspective projection in 2-D case, where d' is a point in 2-D space, which is represented by $$\begin{bmatrix} d_V' \\ d_R' \end{bmatrix},$$

and $\hat{d}$ is the projected point represented by $$\begin{bmatrix} \hat{d}_V \\ \hat{d}_R \end{bmatrix}.$$

Combining these results and yields the closed-form formula for X-ray transform of a box spline in a fan-beam geometry with detector blur:

$$P_{u,\zeta}\{M_\Xi\}(s) = M_{[R_{v(s)^\perp}\Xi',\zeta']}(s) = M_{\Xi'(s)}(s'),$$

and in a cone-beam geometry with detector blur: $P_{u,\tau}\{M_\Xi\}(s,t)=M_{[B_R^T(2,3)\tau']}(B_R^T p(2,3))=M_{Z'(s,t)}(u,v)$ This equation is the analytical closed-form approximation of the Radon transform of a box spline in a fan-beam geometric setting. In a common fan-beam setup, the size of pixels and detector bin width are usually very small and projector-detector distance is much larger so that the approximation made by the effective blur is relatively highly accurate, as is demonstrated in the experiments detailed below.

Continuing with FIG. 5, at step/operation 406, the image is provided. For example, the image reconstruction computing entity 100 may store the image (e.g., in memory 210, 215) and/or provide (e.g., transmit) the image. For example, the image reconstruction computing entity 100 may provide the image such that a user computing entity 110 receives the image. For example, the user computing entity 110 may, responsive to receiving and/or processing the image, cause the image to be displayed via a user interface provided by a display, monitor, screen, and/or the like of the user computing entity 110 and/or in communication with the user computing entity 110. In an embodiment, the image is displayed via the user interface ten minutes or less after the capturing of the projection information/data is completed.

Technical Advantages

Various embodiments of the present invention provide significant technical advantages and address technical challenges of reconstructing an image from projection information/data in a reasonable time period in practical settings (e.g., a clinical setting). For example, an example embodiment reconstructs (e.g., generates) the image based at least in part on the projection information/data and provides and/or displays the image within ten minutes of the capturing of the projection information/data by an imaging machine/device 115. In various embodiments, the image reconstruction can be performed in reasonable time period when then projection information/data is captured (e.g., by the imaging machine/device 115) using low-dose, few view, and/or limited view imaging techniques, such that the radiation that an individual being imaged is exposed to is relatively low and/or minimized.

An important advantage to reconstructing the image from the projection information/data using a convolutional spline process and/or basis is the ability to achieve high performance with on-the-fly computation of the forward and back-projection, eliminating the needs to store the system matrix and/or a look-up table. This is accomplished by efficient evaluation of the box spline on the right hand side of Equation 1 (2D) or 2 (3D). In experiments, a flat detector fan-beam X-ray CT system was simulated with 360 angles over 360° with bin width $\zeta=1$ mm. The image resolutions we choose are 64×64 mm, 128×128 mm, 256×256 mm, 512× 512 mm, 1024×1024 mm, 2048×2048 mm, and the image is an all-ones image for fair comparison (the intensity of each pixel in the image is 1). The detector bin is spaced by $U_s=1$ mm, and the numbers of the detector $N_s$ are 205, 409, 815, and 1627, 3251 and 6499 corresponding to the different sizes of image. As the image size changes, we also choose the different the projector-rotation center distances $D_{po}$ and detector-rotation center distances $D_{so}$ as $(D_{po}, D_{so})=(100$ mm, 100 mm), (200 mm, 200 mm), (400 mm, 400 mm), and (800 mm, 800 mm), (1600 mm, 1600 mm), (3200 mm, 3200 mm). These settings are to adapt for different fields-of-view. All experiments are performed on NVIDIA-GTX 1080 GPU with CUDA-10.0, Intel i7-6800K 6-core CPU with 3.40 GHz.

As shown in FIG. 11, forward and back-projection using the convolution spline process and/or basis results in a significantly faster reconstruction of the image compared to SF and LTRI image reconstruction techniques (e.g., more than 20 times faster, in an example embodiment). Elimination of the need to access a look-up table, leads to high efficiency in GPU implementations. Our method does not store any intermediate data for projections, unlike the precomputed table in LTRI. Therefore, there is not a lot of GPU memory access, which is usually the bottle neck in GPU computing, in our implementation. Also, we notice that the backward projection is always faster than forward projection in both resolutions. The reason for this is that in forward projection, each projection value is weighted sum of several pixels, thus, in CUDA implementation, each kernel thread will execute the atomic add operation that will downgrade the efficiency of parallel computing. This serialized behavior occurs less in back-projection resulting in improved performance. Since there is no GPU version of SF method, we also implement the CPU version of proposed method with Intel Threading Building Blocks (tbb) library that can parallelize code and compare the run time with SF in CPU parallel computing. The results show that the proposed method is faster than SF method overall, and when dealing with larger sizes of images, it achieves image reconstruction 2 times and 2.5 times faster in forward and back-projection respectively.

To evaluate the improvements of accuracy in our method in the actual reconstruction problems, experiments were performed where the measurement was generated by the reference projector and reconstructed with different approximating projectors (e.g., SF, LTRI and convolutional spline). An adaptive steepest descent POCS regularized by total-variation (TV) called ASD-POCS was used and the parameters were adjusted to achieve the highest reconstruction quality for each model. In this experiment, we use Shepp-Logan and the Brain phantom with resolution 128×128 mm and 256×256 mm respectively as the benchmark dataset. The simulated flat detector X-ray system is configured with $N_s=409$, $D_{po}=200$ mm, $D_{so}=200$ mm and $N_s=815$, $D_{po}=400$ mm, $D_{so}=400$ mm. The detector is spaced by $\Delta_s=1$ mm with bin width $\zeta=1$ mm and the projections are uniformly spaced over 360°. The approximating projector made by LTRI results in a less accurate reconstruction (the resolution of look-up table in LTRI is 10000×180). SF makes a slightly more accurate approximation and achieves a little higher quality over LTRI. The convolution spline process and/or basis provides a reconstruction that can achieve the same quality as the one provided by reference projector using ASD-POCS. FIGS. 12 and 13 illustrate the results of the reconstruction. FIG. 12 illustrates the reconstruction of the Shepp-Logan phantom using a reference projector (12A), LTRI (12B), SF (12C), and a forward and back projection method using convolution splines (12D). Table 1 shows the signal to noise ratio (SNR) achieved by each of these methods in reconstructing the image. As can be seen from Table 1, the convolutional spline process and/or basis provides a significant improvement over the LTRI and SF image reconstruction methods. FIG. 13 illustrates a reconstruction of the brain phantom using the reference projector 13A, the difference between the reconstruction provided by the reference projector (illustrated in panel 13A) and the reconstruction provided by LTRI scaled by a factor of 100 in panel 13B, the difference between the reconstruction provided by the reference projector (illustrated in panel 13A) and the reconstruction provided by LTRI scaled by a factor of 100 in panel 13C, and the difference between the reconstruction provided by reference projector (illustrated in panel 13A) and the forward and back method of the present invention (e.g., using convolutional splines) scaled by a factor of 4000 in panel 13D. As shown in FIGS. 12 and 13 and Table 1, the forward and back method (e.g., using convolution splines) provides a better image reconstruction (using the reference projector as a base line) than the LTRI and SF reconstruction methods.

TABLE 1

| Reconstruction Method | SNR |
|---|---|
| Reference Projector | 26.93 dB |
| LTRI | 25.63 dB |
| SF | 25.80 dB |
| Convolutional Spline | 26.93 dB |

Thus, various embodiments, wherein an image is reconstructed from projection information/data using a convolutional spline process and/or basis provide improvements in accuracy and speed over traditional image reconstruction methods.

IV. Conclusion

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for reconstructing an image from projection data by an image reconstruction computing entity, the method comprising:
   receiving, by the image reconstruction computing entity, projection data captured by an imaging device;
   reconstructing, by the image reconstruction computing entity, an image based at least in part on the projection data using a forward and back projection technique employing a convolutional spline process, wherein the convolution spline process comprises:
      computing projected coordinates of 2-D pixels and 3-D voxels on a detector plane,
      computing 1-D footprints on the detector plane of the pixels as a first convolutional spline,
      computing 2-D footprints on the detector plane of voxels as a second convolutional spline,
      approximating 1-D detector blur of pixels by convolving the 1-D footprints with a blur function modeled as a third convolutional spline,
      approximating 2-D detector blur of voxels by convolving the 2-D footprints with a blur function modeled using a fourth convolutional spline, and
      determining the contributions of at least one of the pixels or the voxels to a detector bin using weighted sums of evaluation of the first, second, third, and fourth convolutional splines according to the projected coordinates; and
   providing, by the image reconstruction computing entity, the image such that a user computing entity receives the image, the user computing entity configured to display the image via a user interface thereof.

2. The method of claim 1, wherein the forward and back projection technique employing the convolutional spline process comprises using a box spline basis for performing at least one of a footprint or detector blur computation.

3. The method of claim 1, wherein the forward and back projection technique employing the convolution spline process uses an analytical closed-form calculation of the Radon transform of a box spline in a fan-beam, cone-beam and parallel-beam geometric setting with both flat and arc detectors.

4. The method of claim 3, wherein the analytical closed-form projection of pixel basis in fan-beam geometric setting is a non-separable function: $P_{u,\zeta}\{M_\Xi\}(s)=M_{\Xi'(s)}(s'(s))=M_{[\Xi'_1(s),\Xi'_2(s)]}(s'(s))$.

5. The method of claim 3, wherein the analytical closed-form projection of voxel basis in cone-beam geometric setting is a non-separable function: $P_{u,\tau}\{M_\Xi\}(s,t)=M_{B_R^T\Xi(2,3)}(B_R^T p(2,3))=M_{[B_R^T\xi_1(2,3)B_R^T\xi_2,B_R^T\xi_3]}(u,v)$.

6. The method of claim 3, wherein analytical closed-form projection of pixel basis in parallel-beam geometric setting measured by a detector of size is a non-separable function: $P_{u,\zeta}\{M_\Xi\}(s)=M_{\Xi'(s,p)}(s'(s))=M_{[\Xi'_1(s),\Xi'_2(s),\xi]}(s)$.

7. The method of claim 3, wherein analytical closed-form projection of voxel basis in parallel-beam geometric setting measured by a detector of size $\tau=[\tau_s,\tau_t]$ is a non-separable function: $R_{u,\tau}\{M_\Xi\}(s,t)=M_{Z(s,t)}(s,t)=M_{[B_p^T\Xi(2,3),\tau_s,\tau_t]}(s'(s))$.

8. The method of claim 3, wherein analytical closed-form calculation of projection of pixel basis in fan-beam geometric setting measured by a detector of size is a non-separable function: $P_{u,\zeta}\{M_\Xi\}(s)=M_{\Xi'(s,p)}(s'(s))=M_{[\Xi'_1(s),\Xi'_2(s),\Xi'(s,p)]}(s'(s))$.

9. The method of claim 3, wherein analytical closed-form calculation of projection of voxel basis in cone-beam geometric setting measured by a detector of size $\tau=[\tau_s,\tau_t]$ is a none-separable function: $P_{u,\zeta}\{M_\Xi\}(s,t)=M_{[B_R^T\xi_1(2,3)\ B_R^T\xi_2(2,3),\ B_R^T\xi_3(2,3),\tau'_s,\tau'_t](u,v)}$.

10. The method of claim 3, wherein parameters of the step of computing projected coordinates of pixels and voxels comprises determining a connecting path from a source to the pixels and voxels and computing projected coordinates of the pixels and voxels on the projected plane based at least in part on boundaries of the pixels and the voxels and detector geometry.

11. The method of claim 3, further comprising determining an effective blur width of detector cells by computing the perspective projection of positions of the detector cells.

12. The method of claim 1, wherein the imaging device captured the projection data using a low-dose, few view, or limited view data capture technique.

13. An apparatus comprising at least one processor, a communications interface configured for communicating via at least one network, and at least one memory storing computer program code, the at least one memory and the computer program code configured to, with the processor, cause the apparatus to at least:
receive projection data captured by an imaging device;
reconstruct an image based at least in part on the projection data using a forward and back projection technique employing a convolutional spline process, wherein the convolution spline process comprises:
computing projected coordinates of 2-D pixels and 3-D voxels on a detector plane,
computing 1-D footprints on the detector plane of the pixels as a first convolutional spline,
computing 2-D footprints on the detector plane of voxels as a second convolutional spline,
approximating 1-D detector blur of pixels by convolving the 1-D footprints with a blur function modeled as a third convolutional spline,
approximating 2-D detector blur of voxels by convolving the 2-D footprints with a blur function modeled using a fourth convolutional spline, and
determining the contributions of at least one of the pixels or the voxels to a detector bin using weighted sums of evaluation of the first, second, third, and fourth convolutional splines according to the projected coordinates; and
provide the image such that a user computing entity receives the image, the user computing entity configured to display the image via a user interface thereof.

14. The apparatus of claim 13, wherein the forward and back projection technique employing the convolutional spline process comprises using a box spline basis for performing at least one of a footprint or detector blur computation.

15. The apparatus of claim 13, wherein the forward and back projection technique employing the convolution spline process uses an analytical closed-form calculation of the Radon transform of a box spline in a fan-beam, cone-beam and parallel-beam geometric setting with both flat and arc detectors.

16. The apparatus of claim 13, wherein the imaging device captured the projection data using a low-dose, few view, or limited view data capture technique.

17. A computer program product comprising at least one non-transitory computer-readable storage medium having computer-readable program code portions stored therein, the computer-readable program code portions comprising executable portions configured, when executed by a processor of an apparatus, to cause the apparatus to:
receive projection data captured by an imaging device;
reconstruct an image based at least in part on the projection data using a forward and back projection technique employing a convolutional spline process, wherein the convolution spline process comprises:
computing projected coordinates of 2-D pixels and 3-D voxels on a detector plane,
computing 1-D footprints on the detector plane of the pixels as a first convolutional spline,
computing 2-D footprints on the detector plane of voxels as a second convolutional spline,
approximating 1-D detector blur of pixels by convolving the 1-D footprints with a blur function modeled as a third convolutional spline,
approximating 2-D detector blur of voxels by convolving the 2-D footprints with a blur function modeled using a fourth convolutional spline, and
determining the contributions of at least one of the pixels or the voxels to a detector bin using weighted sums of evaluation of the first, second, third, and fourth convolutional splines according to the projected coordinates; and
provide the image such that a user computing entity receives the image, the user computing entity configured to display the image via a user interface thereof.

18. The method of claim 1, wherein the computed 1-D footprints are exact 1-D footprints on the detector plane and the computed 2-D footprints are exact 2-D footprints on the detector plane.

19. The apparatus of claim 13, wherein the computed 1-D footprints are exact 1-D footprints on the detector plane and the computed 2-D footprints are exact 2-D footprints on the detector plane.

20. The computer program product of claim 17, wherein the computed 1-D footprints are exact 1-D footprints on the detector plane and the computed 2-D footprints are exact 2-D footprints on the detector plane.

* * * * *